US008753705B2

(12) United States Patent
Woo et al.

(10) Patent No.: US 8,753,705 B2
(45) Date of Patent: Jun. 17, 2014

(54) MINERAL-BOUND STARCH COMPOSITIONS AND METHODS OF MAKING THE SAME

(75) Inventors: Kyungsoo Woo, Shawnee, KS (US); Sukh D. Bassi, Atchison, KS (US); Clodualdo C. Maningat, Platte City, MO (US); Girish M. Ganjyal, Atchison, KS (US); Lianfu Zhao, Atchison, KS (US)

(73) Assignee: MGPI Processing, Inc., Atchison, KS (US)

( * ) Notice: Subject to any disclaimer, the term of this patent is extended or adjusted under 35 U.S.C. 154(b) by 898 days.

(21) Appl. No.: 11/146,623

(22) Filed: Jun. 7, 2005

(65) Prior Publication Data

US 2006/0286285 A1 Dec. 21, 2006

(51) Int. Cl.
*A23L 1/05* (2006.01)
*A23L 1/0522* (2006.01)
*C08B 31/00* (2006.01)

(52) U.S. Cl.
CPC .............. *C08B 31/00* (2013.01); *C08B 31/003* (2013.01)
USPC ........................... 426/573; 426/661; 424/488

(58) Field of Classification Search
USPC .................... 426/548, 661, 578, 573; 424/488
See application file for complete search history.

(56) References Cited

U.S. PATENT DOCUMENTS

| | | | |
|---|---|---|---|
| 2,801,242 A | 7/1957 | Kerr et al. | |
| 2,992,215 A | 7/1961 | Bullock et al. | |
| 3,901,725 A * | 8/1975 | Bond et al. ..................... | 127/32 |
| 3,979,286 A | 9/1976 | Wing et al. | |
| 4,280,851 A | 7/1981 | Pitchon et al. | |
| 4,465,702 A | 8/1984 | Eastman et al. | |
| 4,465,704 A | 8/1984 | McCormick-Goodhart et al. | |
| 4,689,228 A | 8/1987 | Rosenberg | |
| 5,855,946 A | 1/1999 | Seib et al. | |
| 5,858,993 A | 1/1999 | Pickart | |
| 6,299,907 B1 | 10/2001 | Seib et al. | |
| 2003/0224031 A1 | 12/2003 | Heier et al. | |
| 2004/0253201 A1* | 12/2004 | Woo et al. ..................... | 424/78.3 |
| 2005/0256306 A1 | 11/2005 | Woo et al. | |

FOREIGN PATENT DOCUMENTS

| | | |
|---|---|---|
| GB | 1520620 | 8/1978 |
| JP | 2002037796 A | 6/2002 |
| WO | WO 9934780 | 7/1999 |
| WO | WO 00/40617 | 7/2000 |
| WO | WO 2004089315 | 10/2004 |
| WO | WO 2004091888 | 10/2004 |

OTHER PUBLICATIONS

Whistler et al., Starch: Chemistry and Technology, 1984, Academic press, Second Edition, 324-333 and364-367.*
European Application No. 06760729.1, Examination Report dated Nov. 4, 2008, 2 pages.
European Application No. 06760729.1, Amendments filed Feb. 20, 2008, 13 pages.
Kim, B.S., et al., "Removal of Heavy Metal Ions From Water by Cross-Linked Carboxymethyl Corn Starch" Carbohydrate Polymers, Applied Sci ence Publishers, Ltd. Barking, GB, vol. 39, No. 3, pp. 217-223, Jul. 1999.
Chabot J.F. et al., "Interaction of Iron Compounds and Starch Granules" Starke 1976, Dep of Food Sci., Stocking Hall, Cornell Univ., Ithaca, New York, vol. 28, No. 8, pp. 264-267, 1976.
Nurul Islam M., et al., "Effect of pH, Temperature and Reaction Time on Calcium Binding by Hydroxypropyl Rice Starches" Starch/Starke 1994 Correspondence Address, B.M.N. Mohd. Azemi, Sch. of Ind. Tech., Univ. Sains Malaysia, Minden, 11800 P. Penang, Malaysia. vol. 46, No. 9, pp. 349-354, 1994.
Kweon D-K, et al., "Adsorption of Divalent Metal Ions by Succinylated and Oxidized Corn Starches" Carbohydrate Polymers, Applied Science Publishers, Ltd., Barking, GB, vol. 46, No. 2, pp. 171-177, Oct. 2001.
PCT/US2006/022217 International Search Report and Written Opinion, Sep. 2006.
PCT/US2006/022217 International Preliminary Report on Patentability Chapter I, Dec. 11, 2007; 6 pages.
European Application No. 06760729.1, Reply Examination Report filed Apr. 30, 2009, 11 pages.
Wang, C.C. et al., "Physiological Properties of Sodium Carboxymethyl Starch" J. of Nutrition, Oct. 1949, pp. 471-481.
European Application No. 06760729.1, Communication Pursuant to Article 94(3) EPC dated Aug. 9, 2010, 5 pages.
European Application No. 06760729.1, Response to EPO Communication dated Feb. 9, 2011, 51 pages.
European Application No. 06760729.1, Communication Pursuant to Article 94(3) EPC dated Feb. 18, 2011, 5 pages.
Japanese Application No. 2008-515902, Office Action dated Jan. 25, 2011, 7 pages.
Canadian Application No. 2,611,431, Office Action dated Jan. 27, 2011, 2 pages.
Abstract of JP 2001-226401, Aug. 21, 2001, 1 page.
Japanese Application No. 2008-515902, Amended claims filed Jul. 27, 2011 in response to Office Action dated Jan. 25, 2011, 8 pages.
Canadian Application No. 2,611,431, Response to Office Action filed Jul. 27, 2011, 13 pages.
Australian Application No. 2006254932, Examiner's First Report dated Mar. 16, 2011, 3 pages.

* cited by examiner

*Primary Examiner* — Jyoti Chawla
(74) *Attorney, Agent, or Firm* — Lathrop & Gage LLP

(57) ABSTRACT

Mineral-bound starch products are provided for enhanced absorption of nutrient minerals. The mineral-bound starch products are prepared by binding biologically active minerals to phosphorylated cross-linked starch. The mineral-bound starch products are stable against heating in hot water followed by washing processes, but able to release bound minerals after digestion.

42 Claims, 23 Drawing Sheets

After 3week

After washing

Before washing

40 %

30 %

20 %

10 % pH 11.5 pH 10.5 pH 9.5

Control

Ferric citrate　　Copper gluconate　　Magnesium chloride　　Manganese sulfate

Potassium iodide　　Sodium citrate　　Zinc chloride　　Nickel oxide

MINERAL-BOUND STARCH COMPOSITIONS AND METHODS OF MAKING THE SAME

FIELD OF THE INVENTION

The present invention relates generally to mineral-bound reversibly swellable granular starches and methods of preparing those products. Individual, chemically cross-linked starch granules interact with minerals to form products that have favorable characteristics. For example, the mineral-bound starches retain minerals throughout hot and cold water hydration cycling, but release the bound minerals after consumption and digestion.

BACKGROUND

Granular cold water swelling starches are well known. These starches can be prepared by suspending wet native starch granules in rapidly moving hot air and subsequently decreasing humidity (U.S. Pat. No. 4,280,851). Alternatively, they can be prepared by heating starch in an excess of water/alcohol with subsequent removal of liquid (U.S. Pat. No. 4,465,702).

When known granular cold water swelling starches are placed in hot or cold water, the granules swell excessively and release starch solubles into the aqueous phase. Upon drying, the individual swollen starch granules collapse and fuse together. Fused granules can be reground, but do not thereafter thicken efficiently and produce a dull taste in food products.

As a consequence of these properties, typical cold water swelling starches have only limited utility in food systems where gelling is to be avoided, e.g., in broths or other watery foods. In such watery systems, the conventional starches swell and gelatinize and release amylose, and upon storage give the food an unappealing texture. In addition, the fact that the known starches are not reversibly swellable (i.e., they are incapable of undergoing successive swelling/drying cycles) limits the utility of conventional starches.

U.S. Pat. No. 6,299,907 describes cross-linked, reversibly swellable granular starches. This type of starch is supplied by MGP Ingredients Inc. of Atchison, Kans. under the name SRS. The starches have a number of novel properties, including the ability to undergo multiple cycles of swelling in hot or cold water and drying while substantially retaining the individuality of starch granules and leaching minimal amounts of starch solubles.

Several attempts have been made to combine starches with minerals for various applications. In general, neutral carbohydrates, such as cellulose or native starch, form weak associations with ions and are regarded as having a poor chelating or metal interaction capacity (Kweon et al 2001, Hood et al 1977). On the other hand, mono-starch phosphate and distarch phosphate ester groups, which are commonly present in phosphorylated cross-linked starch, seem to play an important role in electrostatic attraction of ions in ion exchange absorption using granular starch. Mono- and di-starch phosphate groups provide a strong affinity for metal ions; however, traditionally cross-linked starches (e.g., starches cross-linked in the absence of pre-swelling) bind minerals on their surface. The limited void space in traditionally cross-linked starches makes the acceptance of minerals or ions into the intragranular region difficult.

Islam et al. (1992, 1998) compared native and hydroxypropylated rice starch treated with calcium carbonate. The level of calcium bound to the starch was in the range of 1-116 ppm.

U.S. Pat. No. 4,689,228 discloses a food supplement composition which contains a complex carbohydrate having a molecular weight in a range of from about 750 to about 3500 and a mineral.

U.S. Pat. No. 5,858,993 describes starch-metal complexes useful for accelerating the healing of topical wounds or as hair growth stimulants. The complexes described are prepared from native starch granules which are first solubilized to form a paste and then reacted with relatively high concentrations of copper (II) or tin (II) salts.

U.S. Pat. No. 2,801,242 discloses a method of making cross-linked starches mixed with inorganic flow agents to improve dry flow properties. The residual level of metal was less than 0.1% (starch basis).

U.S. Pat. No. 3,979,286 discloses a composition of cross-linked starch xanthate for removal of heavy metal ions from aqueous solution. Starch is first cross-linked and subsequently xanthated. The water soluble cross-linked starch xanthate reacts with polyvalent metal ions to form water insoluble precipitates, which can be effectively removed from aqueous solution by filtration.

U.S. Pat. No. 2,992,215 discloses a method of making chemically modified starch products useful for ion exchange chromatography. The products retain the original granular starch structure and are prepared by cross-linking the native granular starch with formaldehyde, followed by carboxymethylation or the attachment of 2-(diethylamino)ethyl groups. The ethyl groups are attached by ether linkages or other suitable means of attaching ionic groups to starch molecules.

SUMMARY

Mineral-bound modified starch products and methods of preparing such products are disclosed herein. The starches are chemically cross-linked and bound to nutrient minerals. Useful minerals include, for example, aluminum, calcium, sodium, potassium, iron, iodine, zinc, magnesium, manganese, copper, chromium and nickel. The resultant starches exhibit rapid hydration in cold and hot water, and excellent emulsion stabilization characteristics. The starch products are advantageously used as delivery vehicles for minerals to enhance food, cosmetic and pharmaceutical compositions.

In one aspect, the invention comprises a mineral-bound starch comprising a plurality of individual, cross-linked starch granules with at least one mineral bound both intragranularly and on the surface of the starch granules.

In another aspect, the invention comprises a mineral-bound starch comprising a plurality of individual, cross-linked starch granules capable of undergoing multiple cycles of swelling in 95° C. water for a period of 30 minutes followed by drying at 105° C. to a moisture content of less than about 10% by weight, wet basis, while substantially retaining the individuality of said starch granules, wherein at least one mineral is bound both intragranularly and to the surface of the cross-linked starch granules.

In yet another aspect, the invention comprises a method of preparing a mineral-bound starch comprising the steps of (1) forming a dispersion of starch granules in water, the granules undergoing swelling in said dispersion and having a crystalline phase, (2) adding a cross-linking agent to the dispersion while the granules are swelled, (3) cross-linking the swelled starch granules under conditions of continuous stirring, this cross-linking step being carried out without complete gelatinization of the swelled starch granules, (4) recovering the cross-linked starch granules, and (5) forming a second dispersion comprising the cross-linked starch granules and at least one mineral.

DETAILED DESCRIPTION

Figure 1:
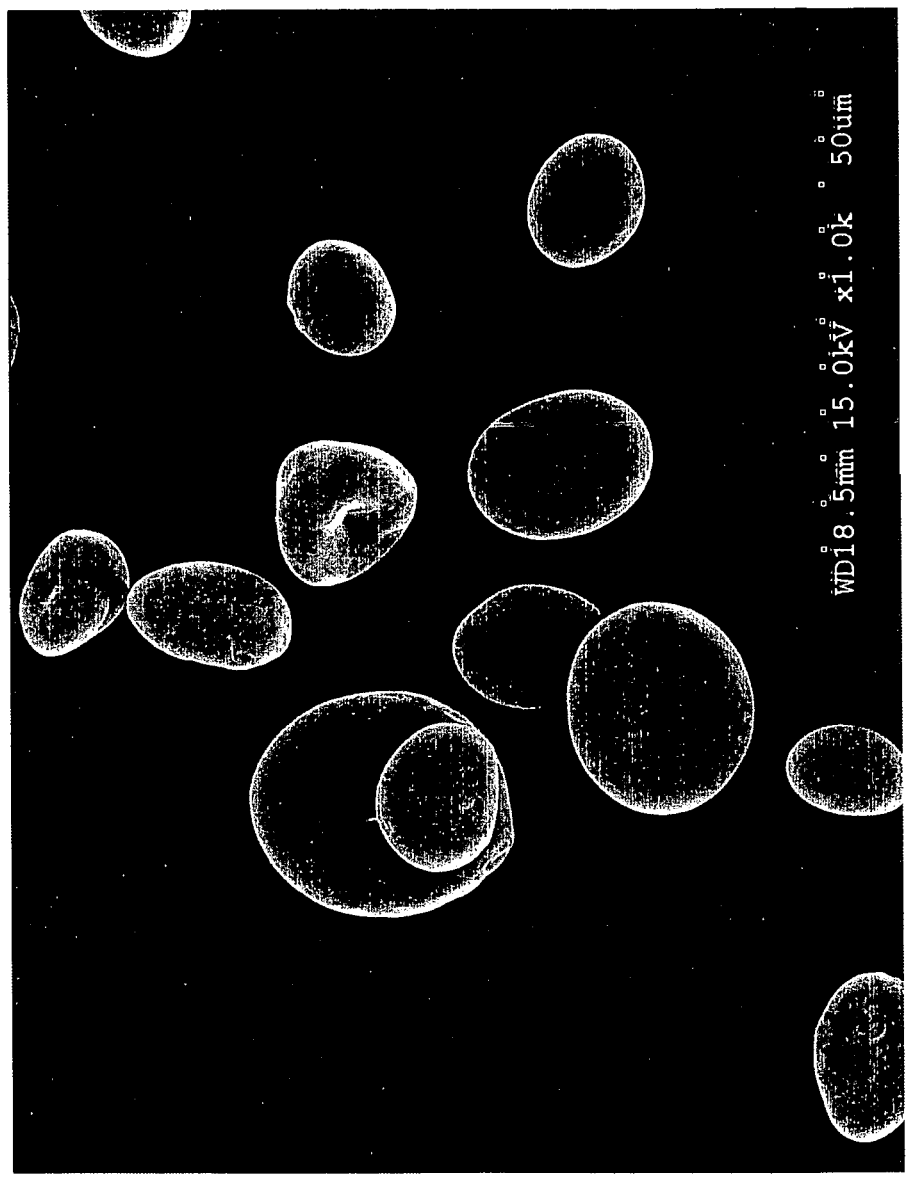
FIG. 1 is a SEM (1000×) of conventional reversibly swellable resistant starch granules (SRS-B).

Starch products bound with biologically active nutrient minerals are formed by reaction of minerals with granular cross-linked starch products. The mineral-bound starches exhibit remarkable nutritional and functional properties. For example, the bound minerals in the starch products are stable against heating in hot water and/or successive washing processes. However, enzymatic hydrolysis of the mineral-bound starch triggers the release of the bound minerals after consumption and makes the minerals available for absorption in the digestive tract. Digestibility of the cross-linked starch products showed greater than 90% hydrolysis by AOAC Total Dietary Fiber Method 991.43.

The mineral-bound starch products readily disperse in cold or hot water, and form stable emulsions in oil/water mixtures without extensive agitation. These properties along with the large surface area and internal void structure formed by pre-swelling the mineral-bound starch products may render them highly suitable for use as thickening, stabilizing, and/or suspending agents, as well as agents for the delivery of biologically active elements such as aluminum, calcium, copper, chromium, iodine, potassium, iron, magnesium, manganese, nickel, potassium, zinc and sodium.

In the preparation of the mineral-bound starch products, minerals are present at levels of from about 0.1-1,000%, more preferably about 1-800%, and most preferably about 1-100% by weight, based upon the total weight of the dry starch.

In one embodiment, the initial cross-linking reaction involves a process of first forming a dispersion of starch granules in water where the granules undergo swelling in their crystalline phase. A cross-linking agent is added to the dispersion while the granules are swelled in order to cross-link the swelled granules. The cross-linking is carried out under conditions that avoid complete gelatinization of the swelled granules. After cross-linking of starch to the desired level, the mixture is neutralized and starch products are washed to remove unreacted salts. The cross-linked products exhibit elevated gelatinization temperatures and decreased enthalpy of gelatinization as compared with the native (unmodified) parent starch.

In one embodiment, the preswelling step is carried out in the presence of a base (such as an alkali metal hydroxide) that promotes swelling and a salt (such as an alkali or alkaline earth metal chloride, sulfate or carbonate) that prevents excessive swelling, that can lead to complete destruction of the granular structure of the starch (i.e., gelatinization). The temperature of the starch dispersion during preswelling is generally 5-10° C. below the starch gelatinization temperature. It is also possible to swell the starch at elevated temperatures, for example at 70-80° C., if high concentrations (greater than 20% based on starch) of salt are used with reduced amounts of base. The hydroxide is normally present at a level of about 1-3% by weight based on starch, while the salt is used at a level of from 5-25% by weight on the same basis. The pH of the preswelling dispersion is generally from about 10-12.3. Useful preswelling/cross-linking conditions and parameters are set forth in U.S. Pat. No. 6,299,907 which is expressly incorporated by reference herein.

During the cross-linking step, the dispersion should have from about 10-40% by weight of starch therein. The cross-linking step generally involves heating to a temperature of from about 30-75° C. for a period of from about 0.1-24 hours, more typically from about 0.5-12 hours. Starches can be chemically cross-linked using a variety of cross-linking agents, such as those selected from the group consisting of sodium trimetaphosphate (STMP), sodium tripolyphosphate (STPP), phosphoryl chloride, epichlorohydrin and mixtures thereof. Where STMP is used as the cross-linking agent, typically from about 2-20% by weight on a dry starch basis is needed to achieve the desired degree of cross-linking. During cross-linking, if too little STMP is employed, the starch will eventually gelatinize. When this occurs, swelling has not been counterbalanced by sufficient inhibition from cross-linking. Increasing the temperature of the cross-linking reaction is a compromise between accelerating the swelling and accelerating the cross-linking reaction, such that gelling of the reaction mixture does not occur prior to sufficient cross-linking in a reasonable period of reaction time.

The cross-linked starch granules may optionally be heated in excess water to melt the crystalline phase of the granules. Wet or dried starch may by used to form an aqueous slurry (10% w/w) that is heated for about 5 minutes. Heating temperatures are generally above 80° C. for non-high amylose starch and above 110° C. for high amylose starch. Heating can be done by a thermal heater, jet cooker, spray cooker, or extruder. The heat treated product may then be cooled, centrifuged and dried in a conventional oven, spray drier, or flash dryer.

Virtually any unmodified starch can be modified according to the methods described herein, including starches selected from the group consisting of cereal, root, tuber and legume. Further starches include those selected from wheat, waxy wheat, corn, waxy corn, high amylose corn, oat, rice, tapioca, mung bean, sago, sweet potato, potato, barley, triticale, sorghum, banana and other botanical sources including waxy, partial waxy, and high amylose variants ("waxy" being intended to include at least 95% by weight amylopectin and high amylose and at least 40% by weight amylose). Chemically, physically or genetically modified forms of starches can also be used. Modification techniques include 1) treatment with chemicals and/or enzymes according to 21 CFR 172.892; 2) physical transformations such as retrogradation (recrystallization), heat treatment, partial gelatinization, annealing and roasting; 3) genetic modifications including gene or chromosome engineering, such as cross-breeding, translocation, inversion and transformation; and 4) combinations of the above.

High levels of cross-linking lead to the formation of resistant starch (U.S. Pat. No. 5,855,946) with decreased digestibility, which substantially limits the release of bound minerals after digestion. For minerals to be effectively released and available for biological needs after ingestion, the mineral-bound starch must be digested more than about 80%, more typically about 90%. Excessive cross-linking of starch also limits the stabilization effect of mineral-bound starch products on mixtures of immiscible solvents. In the absence of proper swelling, binding of minerals may occur only on the surface of the granules. The even distribution of minerals within the granular structure of starch appears to be important to improve functional and nutritional properties for various applications.

Cross-linked starch products may also be oxidized, prior to gelatinization and mineral binding, to form negatively charged starchate anions presenting carboxyl groups. The increased granular charge density resulting from oxidation effects affinity for metal ions and surface interactions with other polymers such as proteins and carbohydrates found in foods, cosmetics and pharmaceutical products. Oxidized products and methods of preparing oxidized cross-linked starch products are disclosed, for example, in commonly-owned and co-pending U.S. patent application Ser. No. 10/843,494. Suitable oxidizing agents may be selected from the group consisting of periodate, chromic acid, permanganate, nitrogen dioxide and sodium hypochlorite.

The oxidation reaction is typically carried out at a pH of 7-12, and more typically from about 10-11. The temperature should be from about 10-50° C. and usually from about 30-45° C. When high-amylase starch is used, the temperature may be in a range of from about 30-80° C. Reaction times are variable depending upon the degree of oxidation desired, but generally range from about 1-24 hours, more typically from about 1-8 hours. Oxidation is normally conducted with continuous agitation. At the end of the reaction, the reaction mixture may be neutralized with acid to pH about 5-7, more typically about pH 6. Thereafter the starch products may be washed with water to remove inorganic salts.

Mineral-bound starch derivatives as described herein may be produced from cross-linked and/or oxidized starches that are subjected to interactions with a single mineral, mixture of minerals or mineral containing residue. The term "mineral" as used herein refers to inorganic substances, such as chemical elements (e.g., $Fe^0$) and compounds (e.g., $FeCl_3$), and also to the individual substituents of a chemical compound, i.e., cations and anions (e.g., $Fe^{3+}$ and $Cl^-$). As such, the term iron, for example, may refer to elemental iron ($Fe^0$), iron cations ($Fe^{2+}$, $Fe^{3+}$), and iron containing compounds (e.g., $FeCl_3$). Minerals are physically trapped and/or chemically bound intragranularly and to the surface of the starch granules. As used herein, the terms "bound" and "binding" shall broadly refer to favorable electrostatic interactions between moieties carrying full or partial charges of opposite sign. For example, the terms bound and/or binding shall refer to Van der Waals interactions, electrostatic attraction, ionic bonding, hydrogen bonding, covalent bonding and the like. Metal cations may bind to phosphate or carboxylate anions and/or non-ionized minerals (i.e., compounds) may be electrostatically attracted to charged starch moieties.

In the final step of mineral binding, the cross-linked and/or oxidized starch products are reacted with appropriate minerals selected from the group consisting of mono and polyvalent metals of Groups 1-16 of the Periodic Table. Preferred metals are aluminum, calcium, copper, iron, magnesium, manganese, nickel, potassium, sodium, chromium, and zinc. Also of use are mixtures of two or more minerals listed in the Code of Federal Regulations (CFR) Title 21, Part 582, Substances Generally Recognized As Safe (GRAS) and CFR Title 21, Part 184, Direct Food Substances Affirmed as Generally Recognized as Safe. Preferred minerals are aluminum sulfate, aluminum ammonium sulfate, aluminum potassium sulfate, aluminum calcium silicate, calcium acetate, calcium alginate, calcium carbonate, calcium chloride, calcium citrate, calcium gluconate, calcium glycerophosphate, calcium hydroxide, calcium iodate, calcium lactate, calcium oxide, calcium pantothenate, calcium propionate, calcium silicate, calcium stearate, calcium sulfate, copper gluconate, copper sulfate, copper iodide, ferric ammonium citrate, ferric chloride, ferric citrate, ferric phosphate, ferric pyrophosphate, ferric sulfate, ferrous ascorbate, ferrous carbonate, ferrous citrate, ferrous fumarate, ferrous gluconate, ferrous lactate, ferrous sulfate, elemental iron, magnesium carbonate, magnesium chloride, magnesium hydroxide, magnesium oxide, magnesium phosphate, magnesium stearate, magnesium sulfate, manganese chloride, manganese citrate, manganese gluconate, manganese sulfate, elemental nickel, potassium alginate, potassium bicarbonate, potassium carbonate, potassium chloride, potassium citrate, potassium hydroxide, potassium glutamate, potassium iodide, potassium lactate, potassium sulfate, sodium acetate, sodium alginate, sodium benzoate, sodium carboxymethyl cellulose, sodium caseinate, sodium hydroxide, sodium bicarbonate, sodium carbonate, sodium citrate, sodium hypophosphite, sodium lactate, sodium metasilicate, sodium propionate, sodium sesquicarbonate, sodium tartarate, sodium pectinate, sodium phosphate, sodium aluminum phosphate, sodium potassium tartarate, sodium tripolyphosphate, sodium thiosulfate, zinc chloride, zinc gluconate, zinc oxide, zinc stearate, and zinc sulfate.

In the preparation of the mineral-bound starch products, minerals are present at levels of from about 0.1-1,000%, more preferably about 1-800%, and most preferably about 1-100% by weight, based upon the total weight of the dry starch. The mineral binding process is carried out at a pH of from about 3-11, and typically from about 5-9 (see FIG. 19). The desired mineral binding temperature is from about 10-85° C., and typically from about 25-45° C. in the case of gelatinized granular cross-linked starch. The reaction time for mineral binding is from about 0.1-12 hours, and typically from about 0.5-5 hours. The mineral binding reaction of cross-linked starch may be conducted with continuous agitation. Thereafter the starch products may be washed with water and dried. The cooking of mineral-bound starch can be accomplished by hydrothermal heating, spray cooking, flash drying, drum drying, or extrusion cooking.

Figure 16:
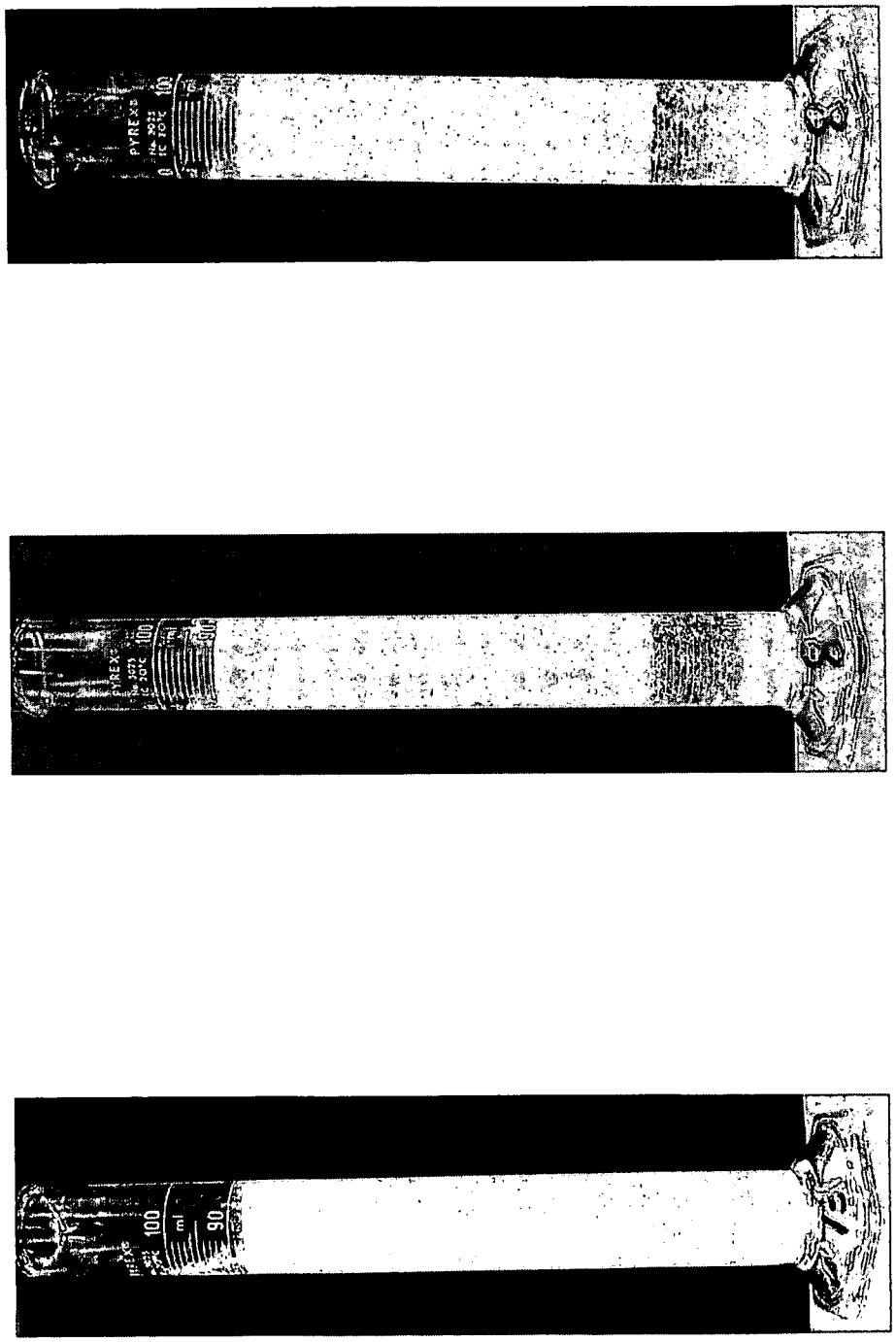
FIG. 16 shows the emulsion stability of calcium-bound SRS-A prepared by cooking with calcium carbonate 10% by weight based on starch.
Figure 17:
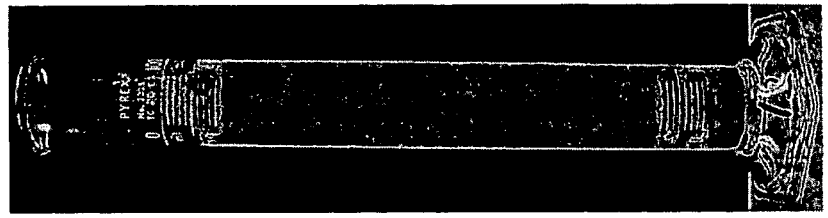
FIG. 17 shows the emulsion stability of calcium-bound PSRS-B without heating.
Figure 17:
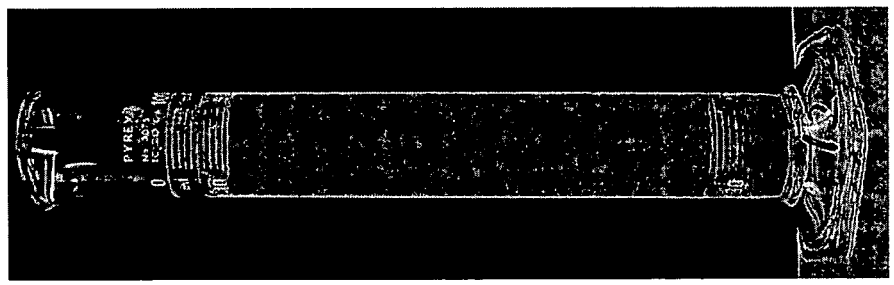
Figure 17:
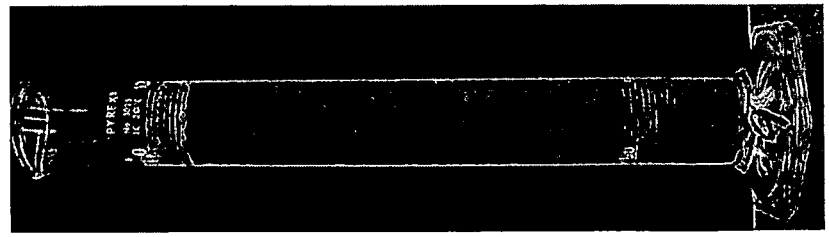

It is apparent that the gelatinized form of granular cross-linked starch products readily bind biologically active minerals at room temperature to form stable emulsions with water and oil (see FIG. 17). In the case of ungelatinized granular cross-linked starch, stable mineral-bound structures may also be conveniently achieved at ambient temperature. However, binding carried out above the gelatinization temperature improves the starch swelling properties in water and the emulsion stability of oil/water mixtures (see FIG. 15). It has been found that the starches form stable emulsions composed of mineral-bound starch, water and oil at concentrations of at least 1 ml/g (see FIGS. 15-23). Moreover, the starches exhibit the foregoing characteristics over extended storage periods, for example at least about 15 days and usually at least about 30 days at room temperature.

Extrusion Cooking

Extrusion is the process of treating materials with high pressure, high shear and high temperature typically for a short period of time in a closed system. The system typically contains a single or twin screw in a jacketed barrel, where heat is supplied externally through the jacketed barrel by steam or by electric heating. The screws rotate either clockwise or counter-clockwise imparting shear and work to the material which is being fed forward along the screws. Towards the end of the screw the material is fed into a die assembly which imparts more shear and also shapes the product into a desired form before expelling it to the atmosphere. During the cooking process in the extruder, many physico-chemical changes occur within the materials. Once the material is expelled into the atmosphere, the product can be cut into different sizes and subjected to various post extrusion treatments such as coloring, flavoring, drying, enrobing, steam treatment, etc. Extrusion is widely used in the food, feed, pharmaceutical and plastic industries for the manufacture of a wide variety of products. Vast literature is available for the extrusion of starches (for example, Harper 1981; Colonna et al., 1989; Kokini et al., 1992; Ganjyal 2004).

Extrusion has been used for encapsulation or binding processes such as: fragranced solid cosmetic compositions based on a destructurized starch delivery system (WO 2004089315), pesticides and crop-yield enhancement products using microencapsulated active ingredients in extruded starch granules (US 2003224031), lactoferrin containing extruded feed supplements (WO 2004091888), starch extrusion as a method for slow-release preparations (Hubert, 2003), and encapsulation of thermolabile active ingredients (WO 9934780). In most of these cases, the starches were destructurized or gelatinized during the extrusion process and a new starch matrix was formed for the encapsulation of the active ingredient.

In the current process, the cross-linked starch granular structure is retained and the granules are bound with different minerals in the extrusion system as described further in the examples. The starch along with the desired quantity of mineral ingredients are preblended in a batch mixer and fed into a preconditioner. Further mixing is performed in the preconditioner with addition of a small quantity of water of about 5 to 10% by weight. The well mixed material is then fed into an extruder barrel, where the mix undergoes high-shear, high-pressure heat treatment, during which the starch granules expand to a certain extent. As the starch granules expand, the minerals enter the opened space and bond with the starch molecules, thus impregnating the starch with the desired minerals. During this process, the proper conditions must be created for the starch granules to open and for the binding process to proceed.

There are various ways that the input conditions to the extruder can be varied, thus providing conditions conducive to the binding process. For example, feed rates of both dry feed and liquids, screw length and/or diameter, screw profile by arrangement of number and type of elements (such as conveying screw elements with different pitches, cut flight screw elements, forward, neutral and reverse lobes, etc), screw speeds, temperature of the barrel by external heating/cooling and die dimensions may be varied.

Various extrusion tests were conducted on a Wenger TX-57™ extruder, which typically contains a preconditioner, a barrel with co-rotating twin-screws, a die set-up, a knife assembly and conveying systems that move the extruded product into a dryer. The screw profile used was a conveying system imparting little shear to the product. The profile consisted of full pitch and three-quarter pitch conveying screw elements, coupled with forward lobes and one final cone screw element. There were no cut flight screw elements used in the profile. A total of five zones were used in the extruder barrel. The feed rate was set to about 60-70% of the maximum capacity of the system. The low-shear screw profile, long barrel and slow feed rate were selected to provide adequate cooking time and space in the system for the starch granules to expand and the metal ions enter the granules.

Figure 2:
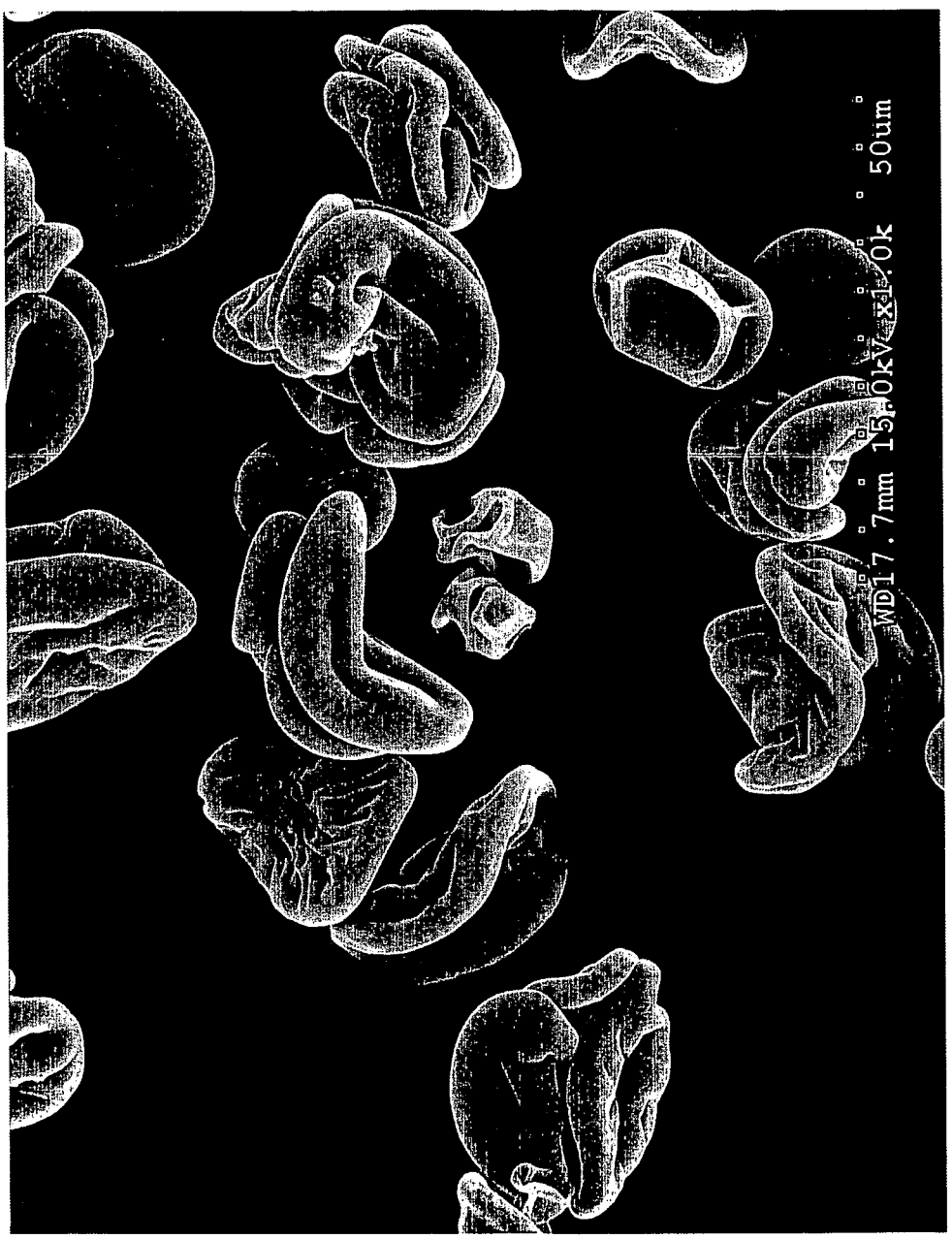
FIG. 2 is a SEM (1000×) of gelatinized and spray dried reversibly swellable resistant starch granules (PSRS-B).
Figure 3:
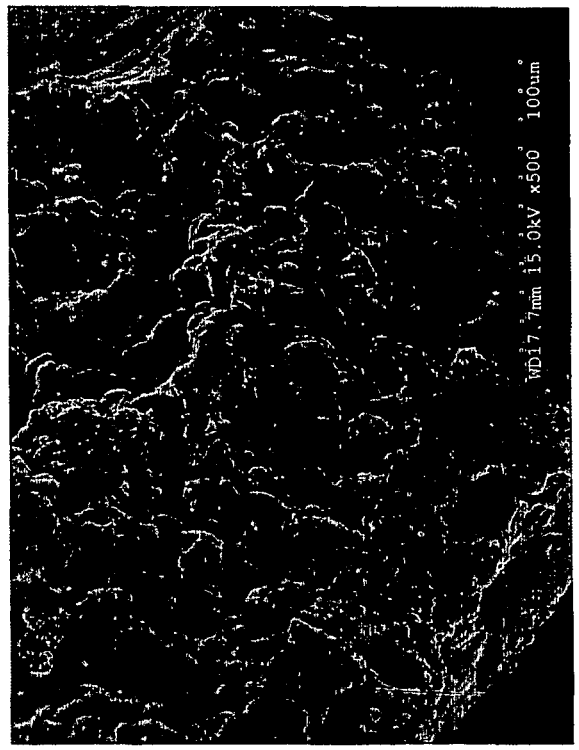
FIG. 3 is a SEM (500×) of calcium-bound SRS-B prepared by cooking with calcium carbonate 10% by weight based on starch.
Figure 3:
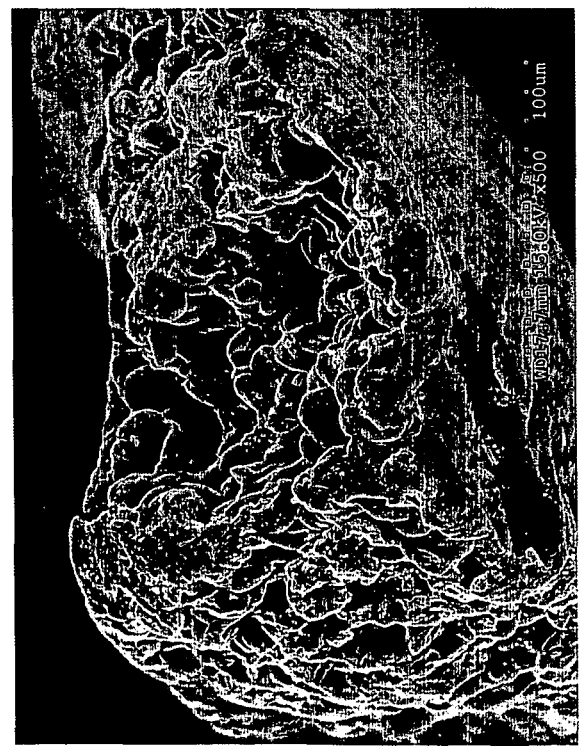
Figure 4:
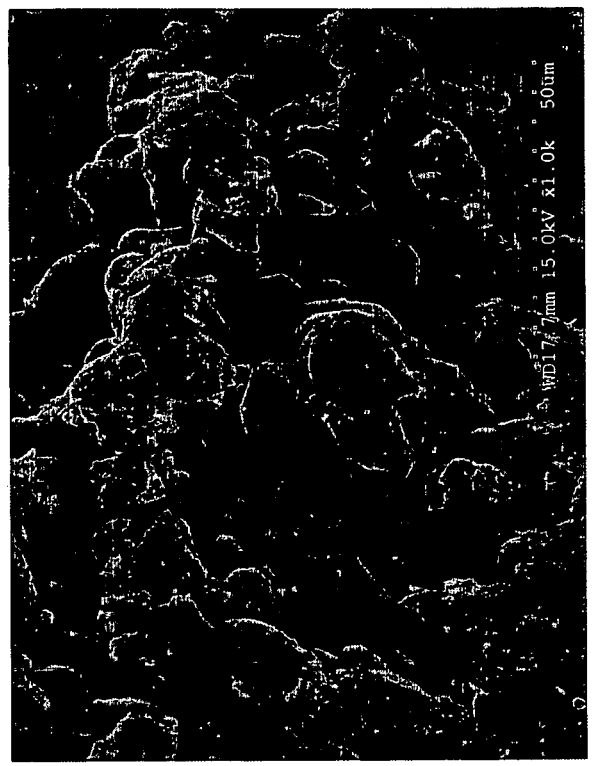
FIG. 4 is a SEM (1000×) of calcium-bound SRS-B prepared by cooking with calcium carbonate 10% by weight based on starch.
Figure 4:
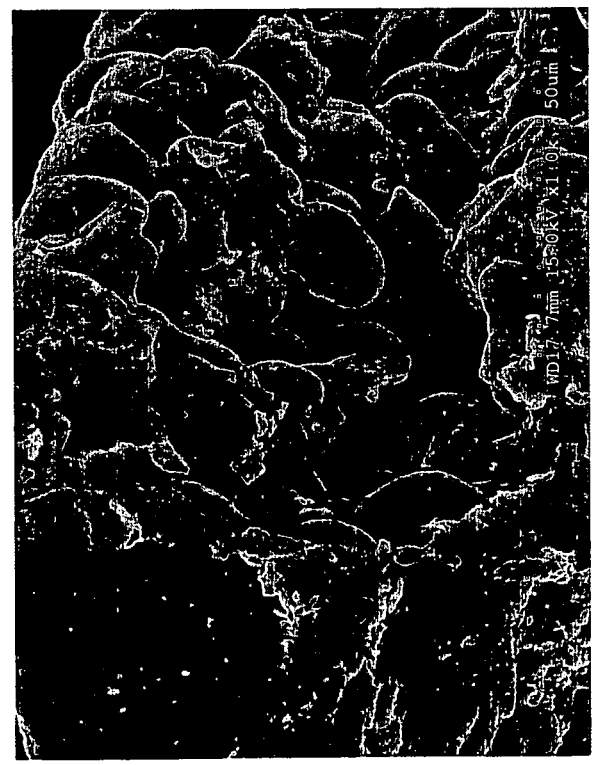
Figure 5:
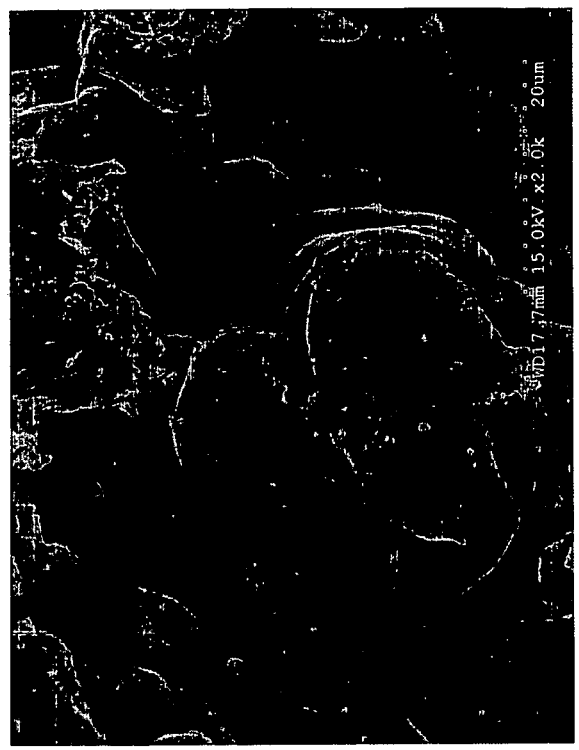
FIG. 5 is a SEM (2000×) of calcium-bound SRS-B prepared by cooking with calcium carbonate 10% by weight based on starch.
Figure 5:
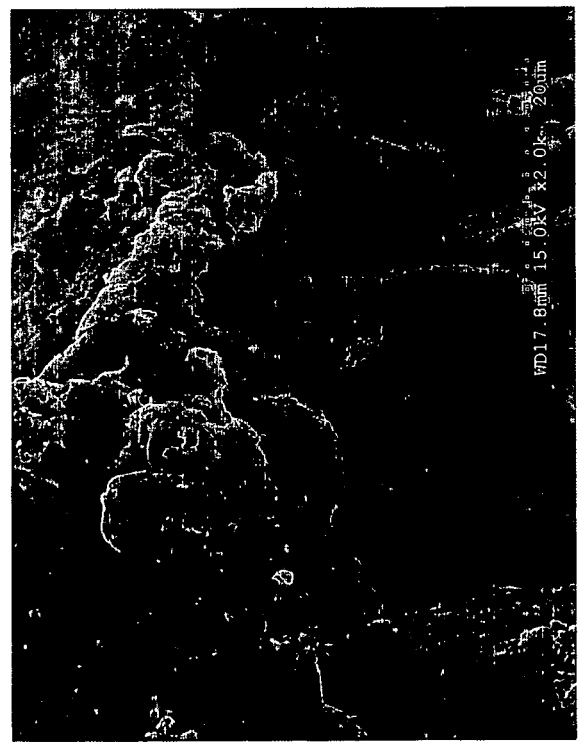
Figure 6:
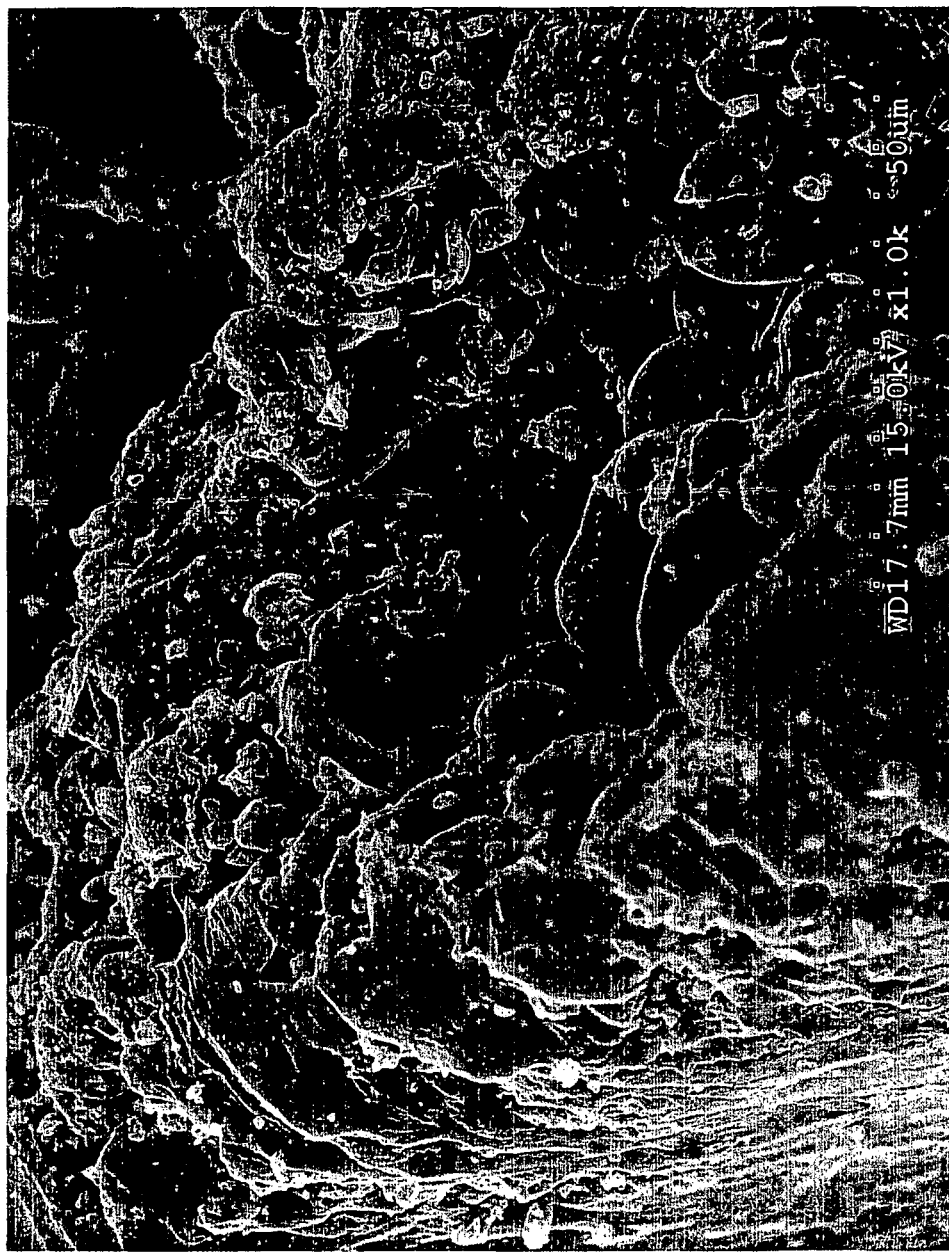
FIG. 6 is a SEM (1000×) of calcium-bound SRS-B prepared by cooking with calcium carbonate 20% by weight based on starch.
Figure 7:
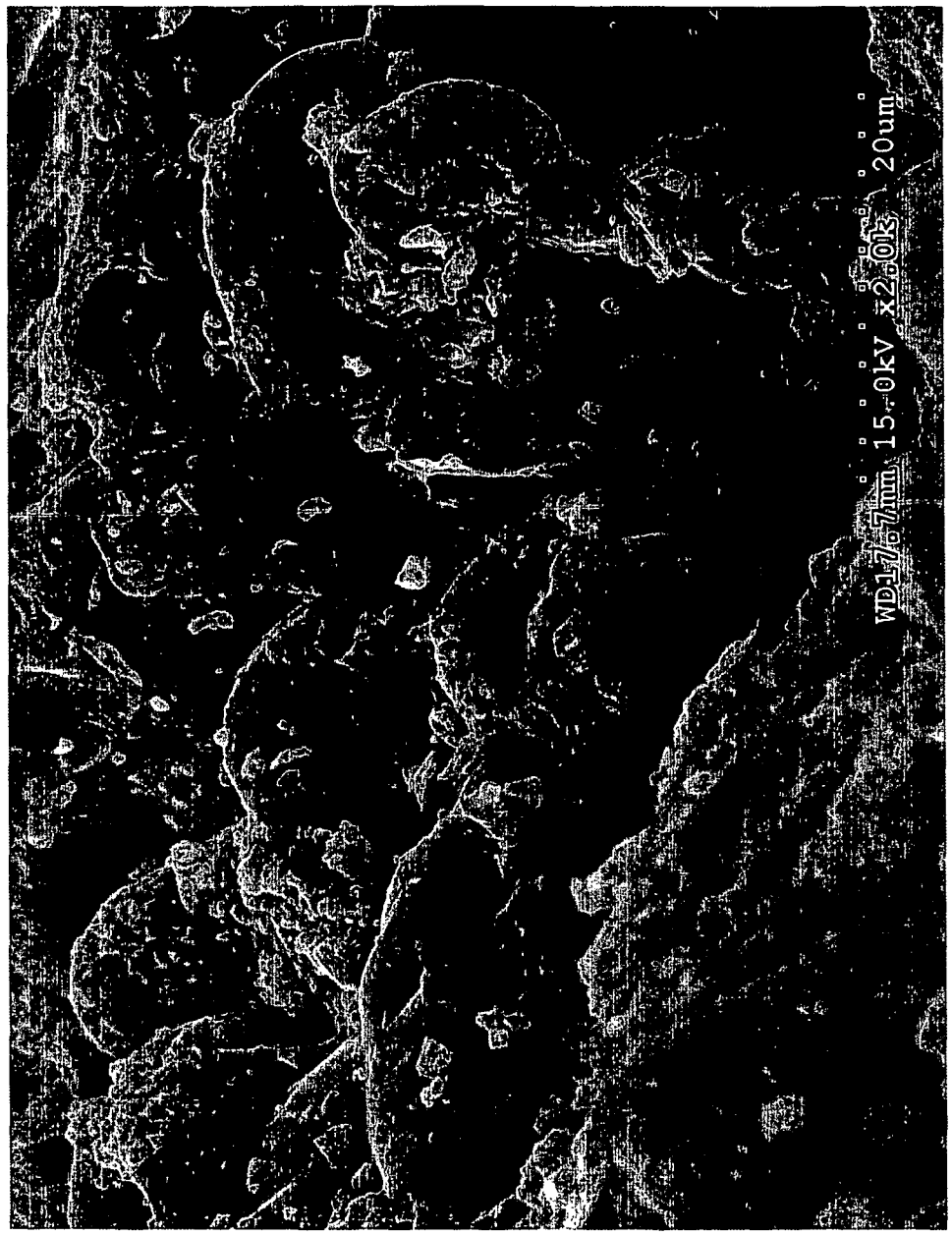
FIG. 7 is a SEM (2000×) of calcium-bound SRS-B prepared by cooking with calcium carbonate 20% by weight based on starch.
Figure 8:
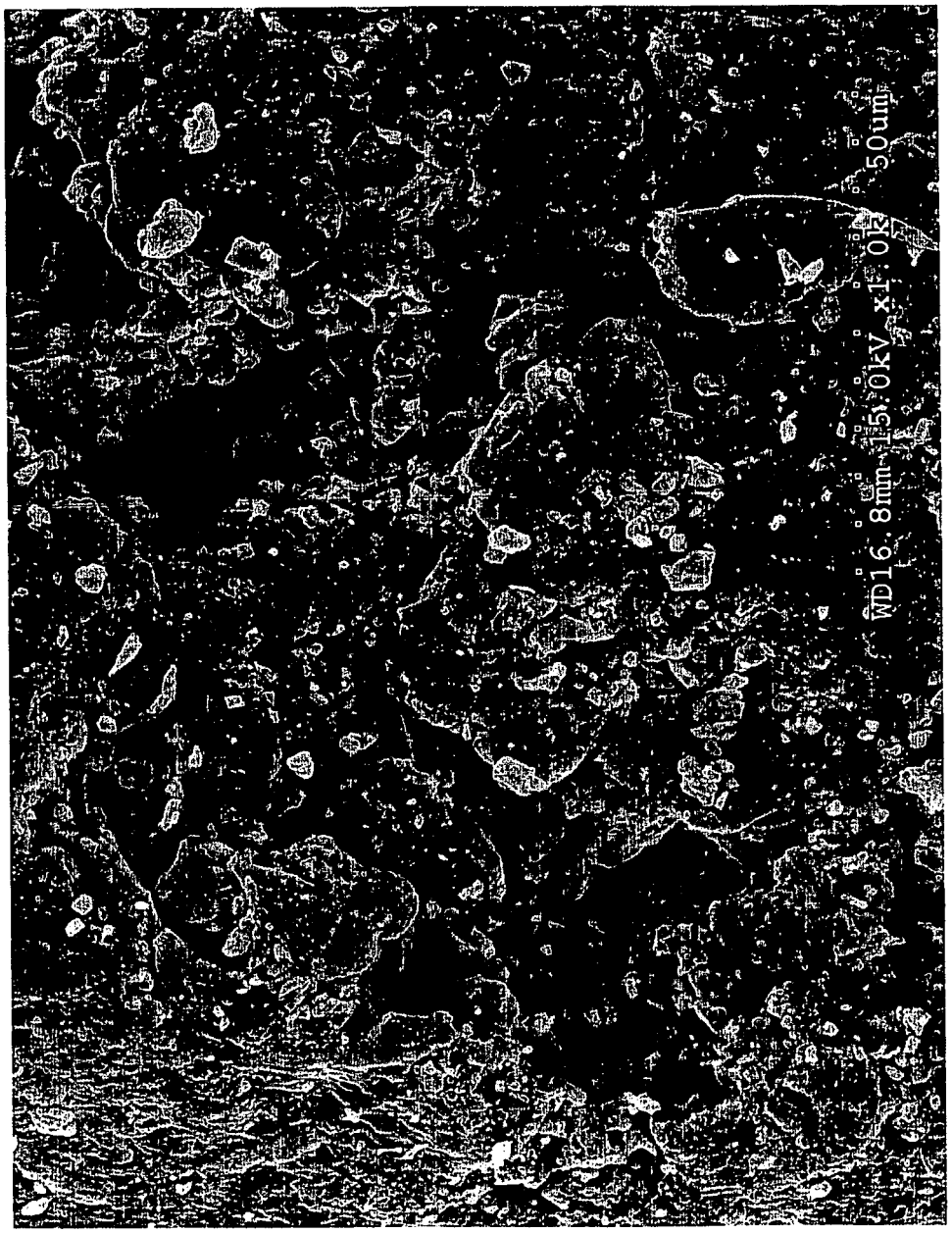
FIG. 8 is a SEM (1000×) of calcium-bound SRS-B prepared by cooking with calcium carbonate 30% by weight based on starch.
Figure 9:
FIG. 9 is a SEM (2000×) of calcium-bound SRS-B prepared by cooking with calcium carbonate 30% by weight based on starch.
Figure 10:
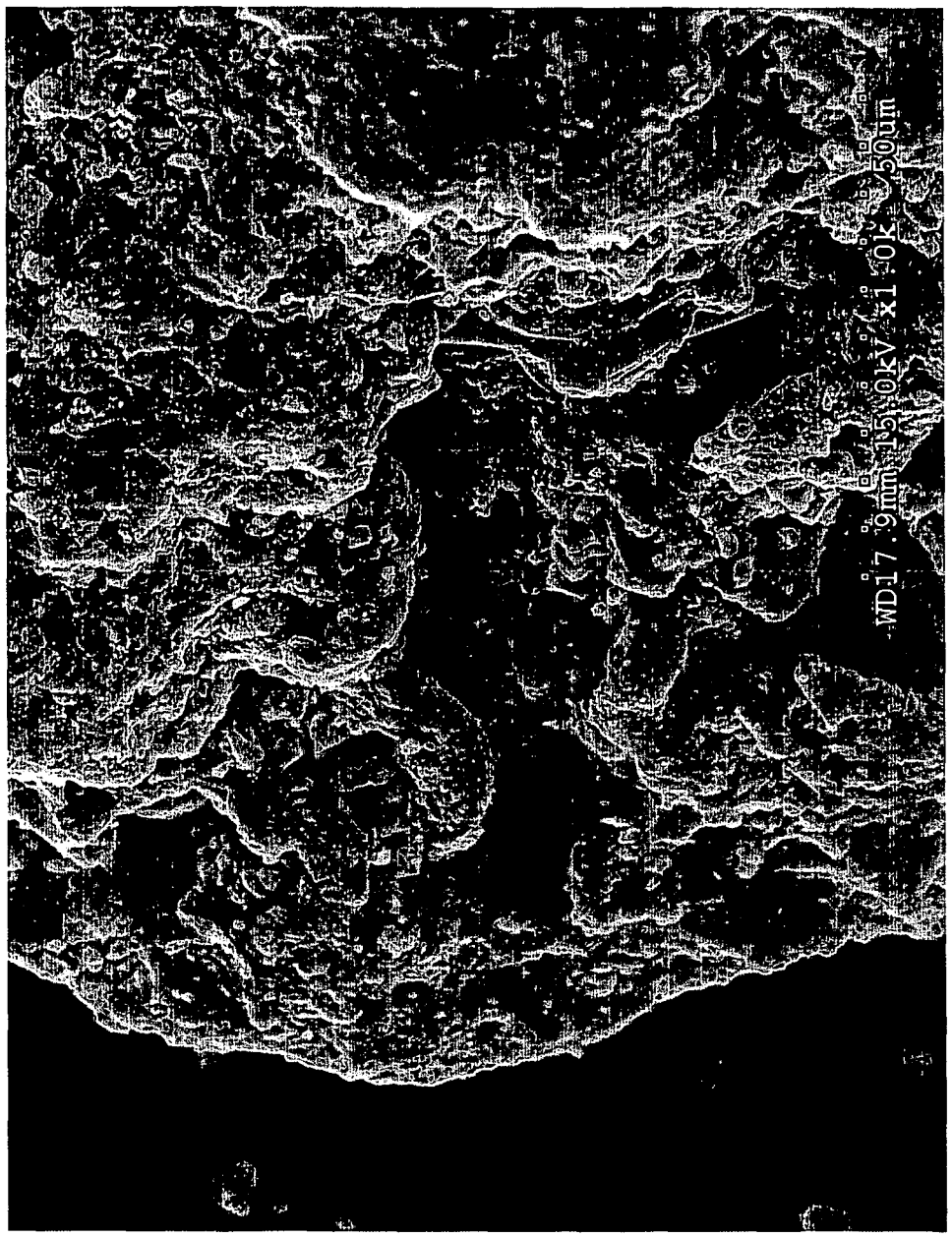
FIG. 10 is a SEM (1000×) of calcium-bound SRS-B prepared by cooking with calcium carbonate 40% by weight based on starch.
Figure 11:
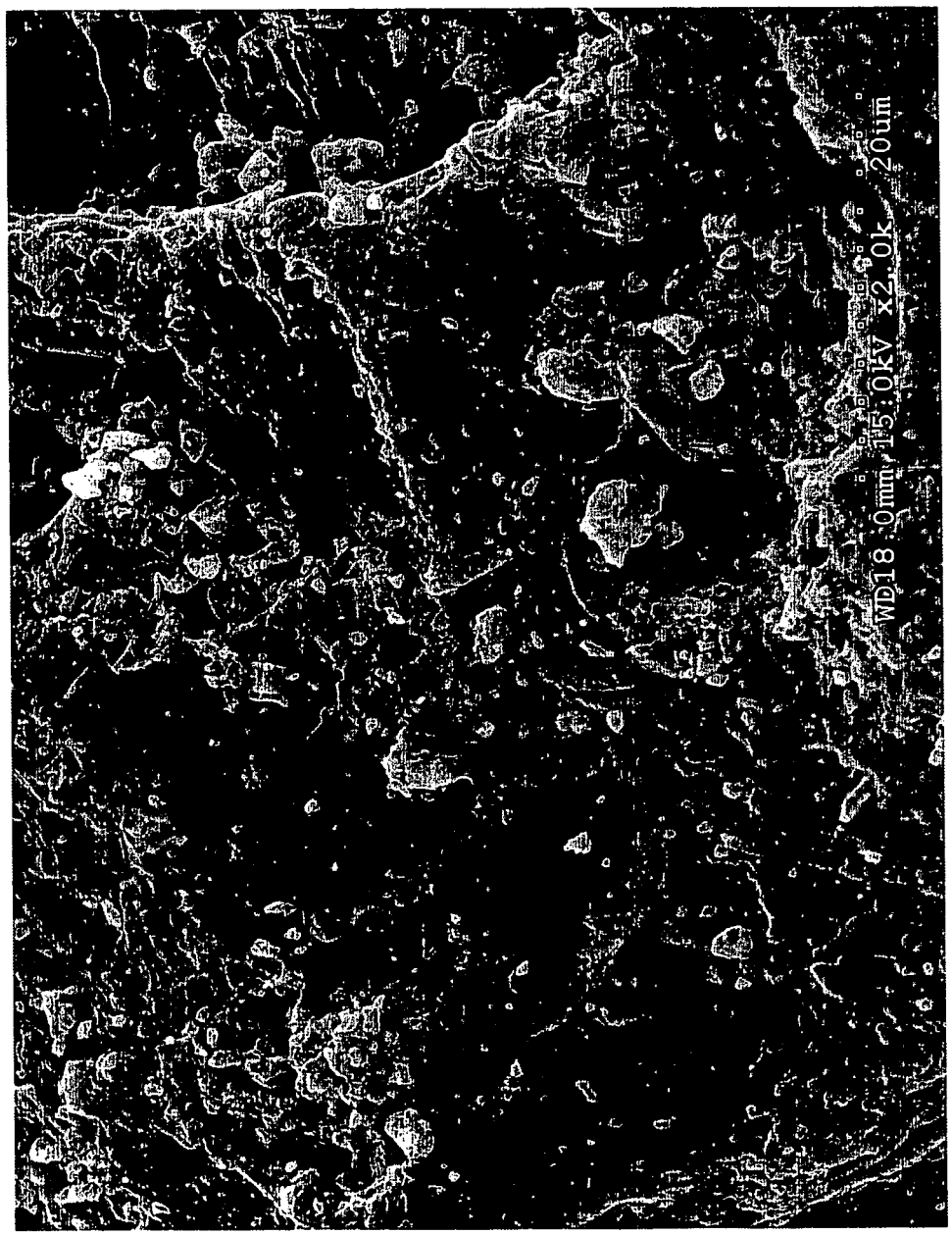
FIG. 11 is a SEM (2000×) of calcium-bound SRS-B prepared by cooking with calcium carbonate 40% by weight based on starch.

FIGS. 1-14 are scanning electron micrographs (SEMs) of a number of starch products and mineral-bound starch products that are described in the following examples. The micrographs illustrate the morphology of the mineral-bound starch products relative to starch products prior to mineral binding shown in FIGS. 1 and 2. FIGS. 15-23 show emulsion stability tests of mineral-bound starch products that are described in the following examples.

The following examples set forth particular granular mineral-bound starch products in accordance with the instrumentalities reported herein, as well as methods of preparing such products. It is to be understood that these examples are provided by way of illustration only, and nothing therein should be taken as a limitation on the scope of what has been invented, which is defined by the claims that follow.

EXAMPLES

In the following examples, ingredient proportions are expressed as weight relative to dry starch unless otherwise indicated. SRS-A, SRS-B, PSRS-B and SRS-C were made by the following procedures:

SRS-A:

Wheat starch (100 parts, dry basis) was dispersed in 233 parts of water with 2 parts of sodium sulfate and mixed. After mixing for 30 minutes, sodium hydroxide (1.5 parts) was added. The reaction mixture was heated to 45° C. and continuously mixed at that temperature for 1 hour. For efficient cross-linking, 3.8 parts of sodium trimetaphosphate, 0.038 parts of sodium polyphosphate and 3 parts of sodium sulfate were added together. After further mixing for 20 hours at 45° C., the slurry was neutralized to pH 6.5 with dilute 1.0 N hydrochloric acid and cooled to 25° C. Starch was isolated by washing with water and spray drying.

SRS-B:

Wheat starch (100 parts, dry basis) was dispersed in 400 parts of water with 3 parts of sodium sulfate and mixed. After mixing for 30 minutes, sodium hydroxide (1.8 parts) was added. The reaction mixture was heated to 45° C. and continuously mixed at that temperature for 15 hours. The reaction mixture was cooled to 35° C. and additional sodium hydroxide (0.7 parts) was added. The reaction mixture was heated to 45° C. and continuously mixed at that temperature for 5 hour. For efficient cross-linking, 5.0 parts of sodium trimetaphosphate and 0.0004 parts of sodium polyphosphate were added together. After further mixing for 16 hours at 45° C., the slurry was neutralized to pH 6.5 with dilute 1.0 N hydrochloric acid and cooled to 25° C. Starch was isolated by washing with water and spray drying.

PSRS-B:

Pre-swollen/cross-linked starch, prepared as described above for SRS-B, was dispersed in 100 ml of water and heated at 95° C. for 10 minutes to melt the crystalline phase.

SRS-C:

Pre-swollen/cross-linked starch, prepared as described above for SRS-A, (300 parts, dry basis) was dispersed in 700 parts of water and mixed for 30 minutes. The dispersion was warmed to 45° C. and pH was adjusted to 11.0 with 1M sodium hydroxide. Sodium hypochlorite 7.5% (dry starch basis) was added to the slurry and continuously stirred for 16 hours at 45° C. The slurry was adjusted to pH 6.0 with 1.0 N hydrochloric acid and then cooled to room temperature (25° C.). The ungelatinized starch was washed with water to remove inorganic salts and recovered by spray drying.

Example 1

Mineral binding was effected by dispersing 10 parts reversibly swellable starch (50 g, dry basis) in 100 parts water (100 ml) with 1 part calcium carbonate (5 g). The dispersion was warmed to 85° C. and maintained at that temperature for 1 hr with continuous stirring. The starch slurry was dried in an oven at 40° C. The starch products were washed two times by mixing with excess water (100 ml), centrifuging (3,000 g for 10 min), decanting the supernatant and drying at 40° C. The product before and after washing was compared in emulsion stability tests.

Testing

Five grams mineral-bound starch was dispersed in 100 ml of a 1:1 mixture of distilled water and vegetable oil (e.g., soybean oil) at room temperature (approximately 25° C.) in a 250 ml beaker (e.g. Corning Pyrex graduated cylinder #3025-100) and then heated to 85° C. and stirred continuously for 30 minutes. The mineral-bound starch/oil/water mixture was then transferred to a 100 ml graduated cylinder (e.g. Corning Pyrex beaker #3062-100). The water/oil/mineral-bound starch dispersion had a creamy appearance at 85° C. The dispersion was then allowed to sit for 24 hours at room temperature (approximately 25° C.). Three fractions formed: a water/mineral-bound starch fraction, a water fraction and a mineral-bound starch/oil fraction (listed from the bottom up in the cylinder). After the 24 hours, the swollen volume of each of the three fractions in the cylinder was measured. Swollen volume ratios for each of the three fractions was determined by measuring the swollen volume (in milliliters) of a fraction and dividing this by the dry weight of the starch (in grams).

Figure 15:
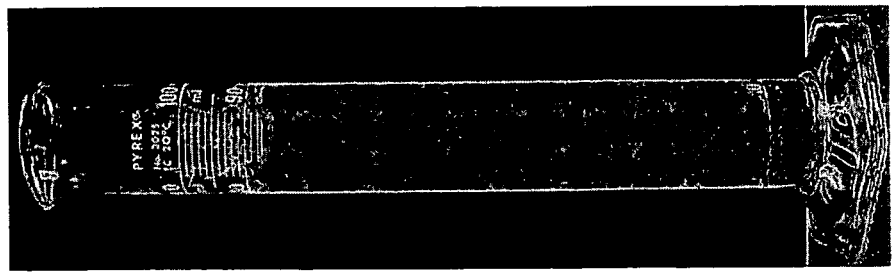
FIG. 15 shows the emulsion stability of calcium-bound SRS-B prepared by cooking with calcium carbonate 10% by weight based on starch.
Figure 15:
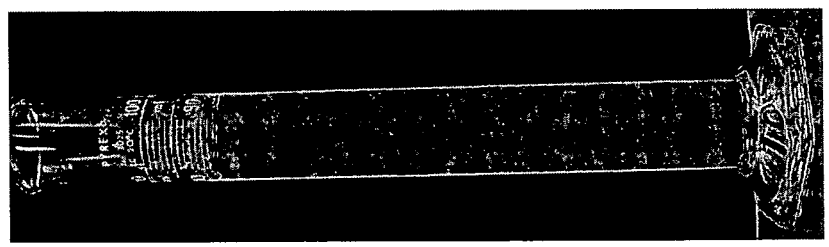
Figure 15:
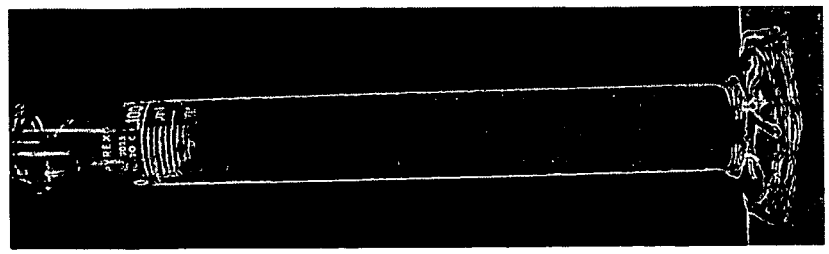

The binding level of calcium after washing was measured by the AOAC 990.08 method, which called for ashing the sample at 550° C. in a muffle furnace overnight. The residue was digested in hydrochloric acid solution and quantitation was performed by inductively coupled plasma (ICP). In each mineral-bound starch product, calcium was successfully bound and essentially no loss occurred after washing with copious amounts of water. In emulsion stability tests, both calcium-bound SRS-A and SRS-B showed excellent stability and formed stable emulsions of calcium-bound starch, water and oil. FIGS. 15 and 16 show the emulsion stability of calcium-bound SRS-B and calcium-bound SRS-A, respectively. The emulsions were stable during storage at room temperature for approximately 3 weeks with essentially no phase separation.

| | Calcium content (mg/100 g starch) after washing |
|---|---|
| SRS-A | 3480 |
| SRS-B | 3460 |

Example 2

The same ratio of starch and calcium carbonate (10:1) used in Example 1 was mixed in water and cooked. The cooked starch with calcium was dried at 105° C. in an oven overnight. After cooling, the starch products were washed two times with excess water (10 ml) to remove unbound residues and dried at 40° C. in an oven. The bound level of calcium was measured according to method AOAC 990.08.

| | Calcium content (mg/100 g starch) after washing |
|---|---|
| SRS-A | 3520 |
| SRS-B | 3490 |

Example 3

Ten parts PSRS-B were dispersed in 100 parts water and 1 part calcium carbonate was added. After mixing for 1 h at room temperature, the product was dried at 40° C. in an oven. The dried starch product was washed and dried using the method described in Example 1. Calcium was efficiently bound with PSRS-B without heating and the mineral-bound starch product showed excellent emulsion stability, comparable to the calcium-bound SRS-B and calcium-bound SRS-A prepared by heating at 85° C. for 1 h. FIG. 17 shows the emulsion stability of calcium-bound PSRS-B. The emulsion formed by calcium-bound PSRS-B was stable during storage at room temperature for 3 weeks.

| Calcium content (mg/100 g starch) after washing | |
| --- | --- |
| PSRS-B | 3750 |

Example 4

Figure 18:
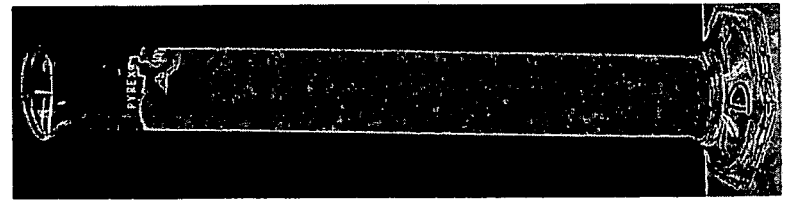
FIG. 18 shows the emulsion stability of calcium-bound PSRS-B prepared with various levels of calcium carbonate.
Figure 18:
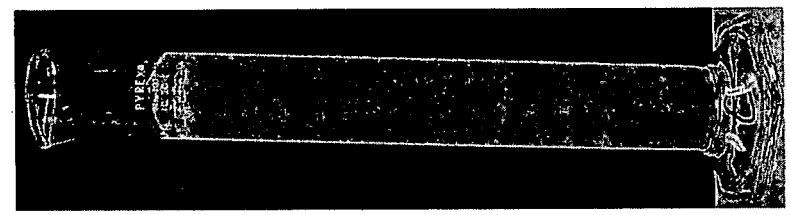
Figure 18:
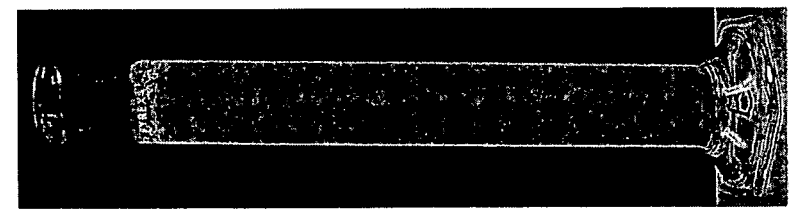
Figure 18:
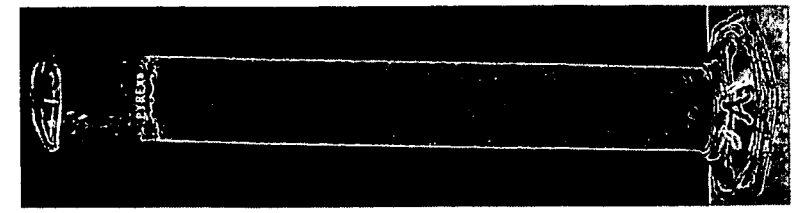

Calcium was bound with PSRS-B using one part calcium carbonate according to the method of Example 1. Ten parts PSRS-B were dispersed in 100 parts water and calcium carbonate was added. The same procedure was followed for mixtures containing two, three and four parts, respectively, of calcium carbonate. For samples made with three and four parts calcium carbonate, 2 parts water were added for ease of dispersion and homogeneous mixing. Calcium was successfully bound in the starch products and remained bound after washing twice with copious amounts of water. In emulsion stability tests, the products showed excellent emulsion stability for calcium-bound starch, water and oil emulsions. FIG. 18 shows emulsion stabilities of calcium-bound PSRS-B prepared with various levels of calcium carbonate. Scanning electron microscopy (SEM) showed that association of starch granules increased with increased levels of calcium carbonate. FIGS. 3-11 show SEMs of calcium-bound SRS-B prepared with various quantities of calcium carbonate, at magnifications ranging from 500× to 2000×.

| PSRS-B:Calcium carbonate | Calcium content (mg/100 g starch) | |
| --- | --- | --- |
| | Before washing | After washing |
| 10:1 | 3410 | 3480 |
| 10:2 | 6170 | — |
| 10:3 | 8410 | 8380 |
| 10:4 | 10400 | 10100 |

Example 5

Figure 19:
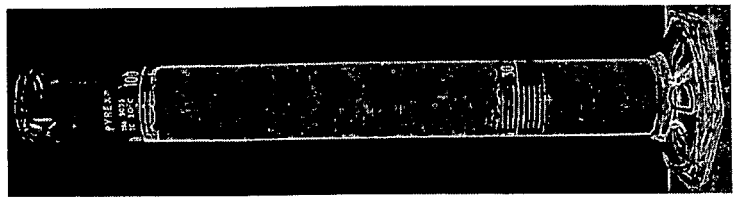
FIG. 19 shows the emulsion stability of calcium-bound PSRS-B prepared at various pH levels.
Figure 19:
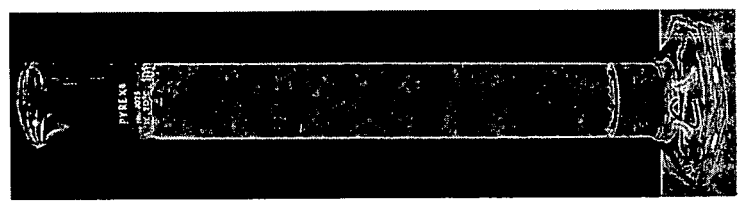
Figure 19:
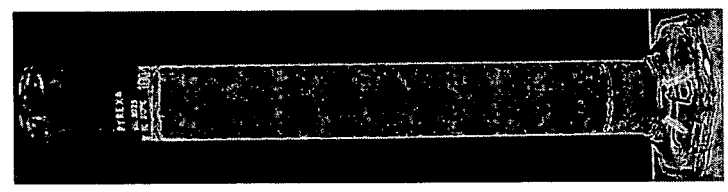
Figure 19:
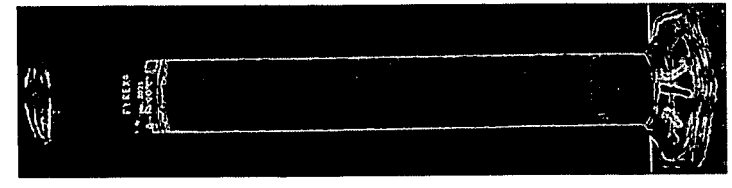

According to the method of Example 1, calcium was bound with SRS-B at various pH levels. 8.9 parts SRS-B were dispersed in 100 parts water and 1 part calcium carbonate was added. The dispersion was warmed to 85° C. and maintained at that temperature for 1 hr with continuous stirring. The starch products were washed twice with excess water (10 ml) to remove unbound residues and dried at 40° C. In emulsion stability tests, products showed excellent emulsion stability and formed stable emulsions of calcium-bound starch, water and oil. FIG. 19 shows emulsion stabilities of calcium-bound PSRS-B prepared at various pH levels.

| pH | Calcium content (mg/100 g) |
| --- | --- |
| Control | 4300 |
| 9.5 | 4180 |
| 10.5 | 4530 |
| 11.5 | 4290 |

Example 6

Figure 20:
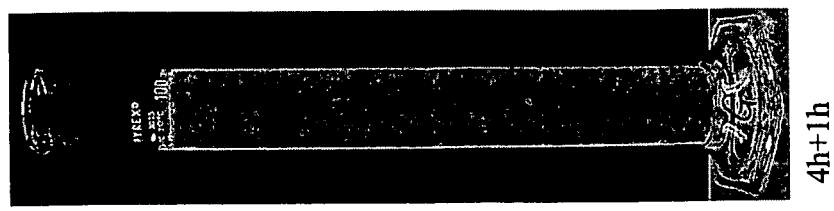
FIG. 20 shows the emulsion stability of calcium-bound PSRS-B prepared by various mixing methods.
Figure 20:
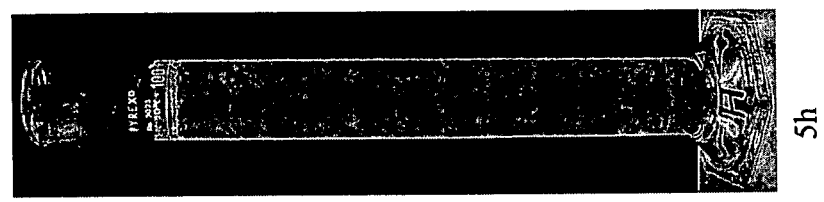
Figure 20:
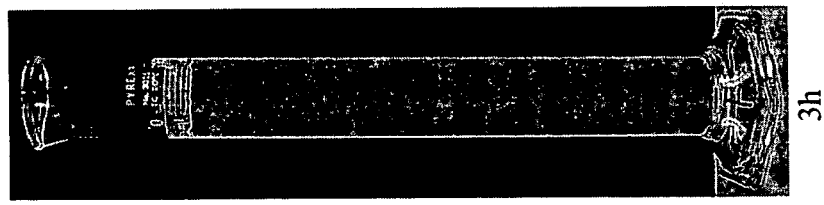
Figure 20:
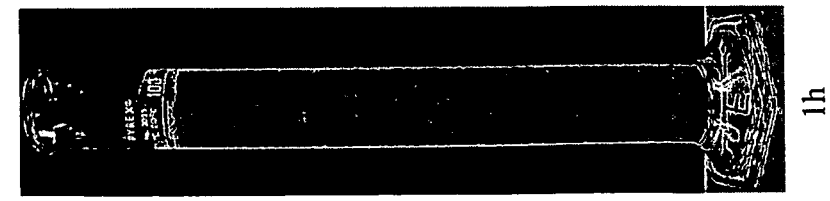

According to the method of Example 1, calcium binding was performed using various mixing times. Mineral-bound starch products were prepared by reacting starch and calcium carbonate (8.9:1) in water. The reaction mixture was cooked at 85° C. for various time periods (1, 3 and 5 h). The effect of premixing in cold water (4 h) before heating for 1 h at 85° C. was also tested. The mineral-bound starch products were washed twice with excess water (10 ml) to remove unbound residues and dried at 40° C. In emulsion stability tests, products showed excellent emulsion stability and formed stable emulsions of calcium-bound starch, water and oil. FIG. 20 shows emulsion stabilities of calcium-bound PSRS-B prepared by various mixing methods.

| Time | Calcium content (mg/100 g) |
| --- | --- |
| 1 h | 4360 |
| 3 h | 3620 |
| 5 h | 4390 |
| 4 h & 1 h | 4360 |

Example 7

Figure 21:
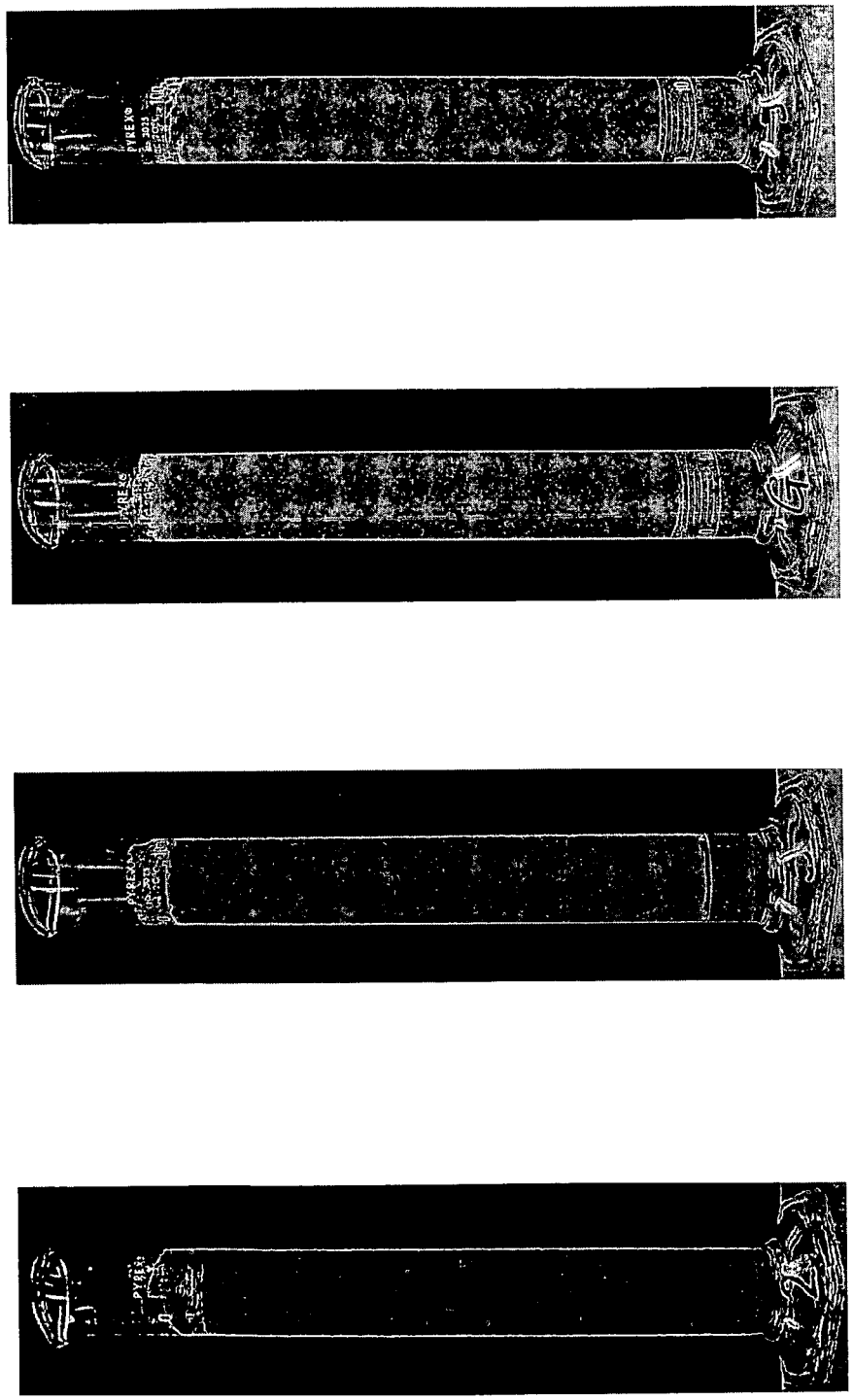
FIG. 21 shows the emulsion stability of calcium-bound PSRS-B prepared with a high level of calcium carbonate.

Calcium binding was performed with various levels of calcium carbonate. Ten parts SRS-B were mixed with 100 parts water and calcium carbonate (20, 50, 80 parts) was added. For ease of dispersion and homogenous mixing, 20, 40, 80 and 140 parts additional water were added to the starch slurries with continuous mixing. After heating at 85° C. for 1 h the mineral-bound starch product was isolated by centrifugation (3,000 g for 10 min), washed twice with copious amounts of water and dried at 40° C. In emulsion stability tests, mineral-bound starch products showed excellent emulsion stability and formed stable emulsions of calcium-bound starch, water and oil. FIG. 21 shows emulsion stabilities of calcium-bound PSRS-B prepared with various levels of calcium carbonate.

| Calcium carbonate (%, based on starch) | Calcium content (mg/100 g) |
| --- | --- |
| 200% | 24,800 |
| 500% | 35,300 |
| 800% | 35,800 |

Example 8

According to the method of Example 1, calcium binding was performed with SRS-C. Mineral-bound starch products were prepared by reacting SRS-C and calcium carbonate (8.9:1) in water. The reaction mixture was cooked at 85° C. for 1 h. The mineral-bound starch products were washed twice with excess water (10 ml) to remove unbound residues and dried at 40° C.

| | Calcium content (mg/100 g) |
| --- | --- |
| SRS-C | 3,540 |

Example 9

Calcium-bound starch was prepared with SRS-A and calcium carbonate by an extrusion process using the parameters shown in the table below. Ten parts SRS-A were mixed with 1 part calcium carbonate. In emulsion stability tests, mineral-bound starch products showed excellent emulsion stability and formed stable emulsions of calcium-bound starch, water and oil.

| Extrusion conditions | |
| --- | --- |
| Feed Rate | 160 lb/hr |
| Extrusion Barrel Temperature Profile | 91-160-180-200-220° F. |
| Extrusion Pressure | 750 psi |
| Extrusion Motor Load | 18% |
| Extruder Speed | 450 rpm |
| Moisture in the cylinder | 16 lb/hr |
| Moisture in the barrel | 29 lb/hr |
| Calcium content (mg/100g starch) | |
| Extruded SRS-A | 3270 |

Example 10

Figure 12:
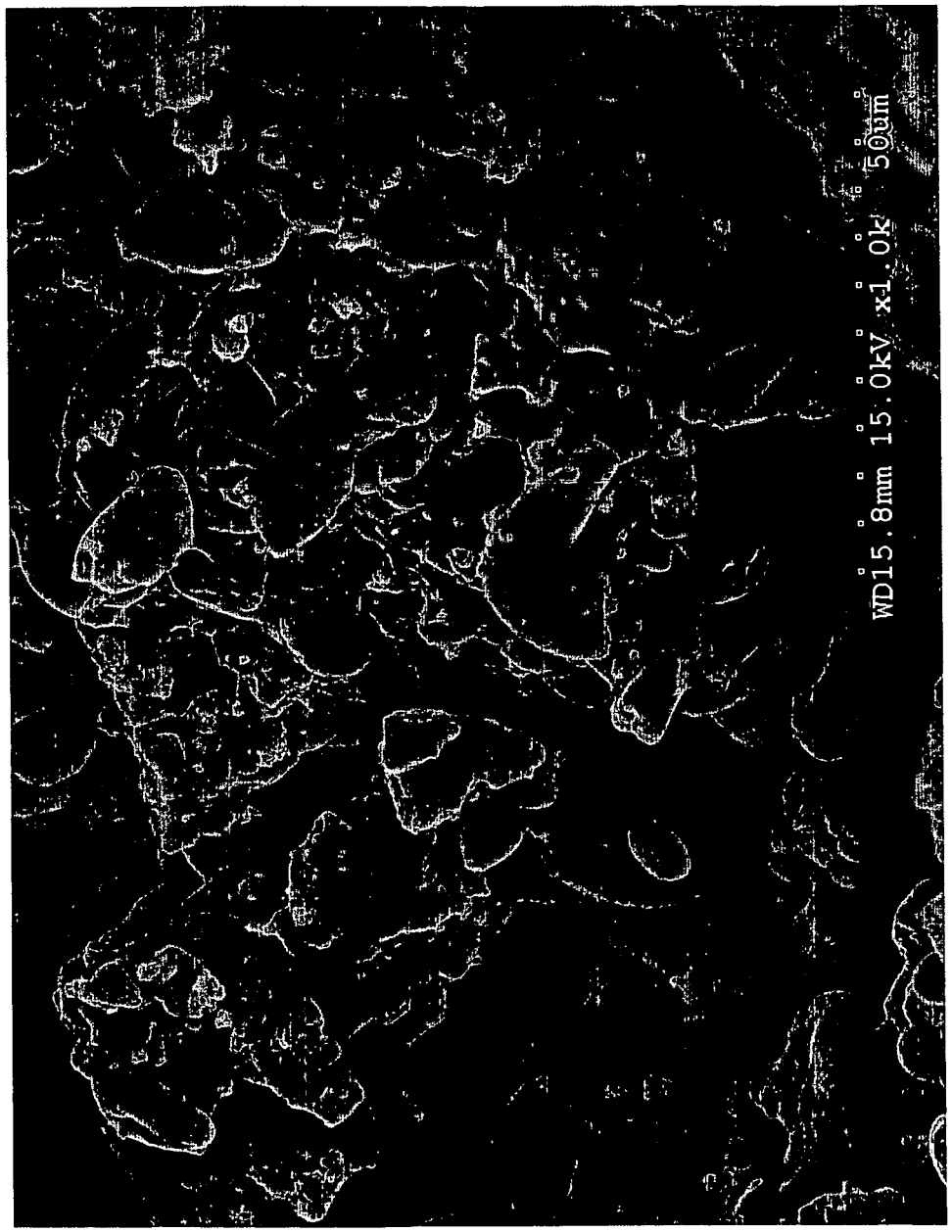
FIG. 12 is a SEM (1000×) of calcium-bound SRS-B prepared by extrusion with 10% calcium carbonate by weight based on starch.
Figure 13:
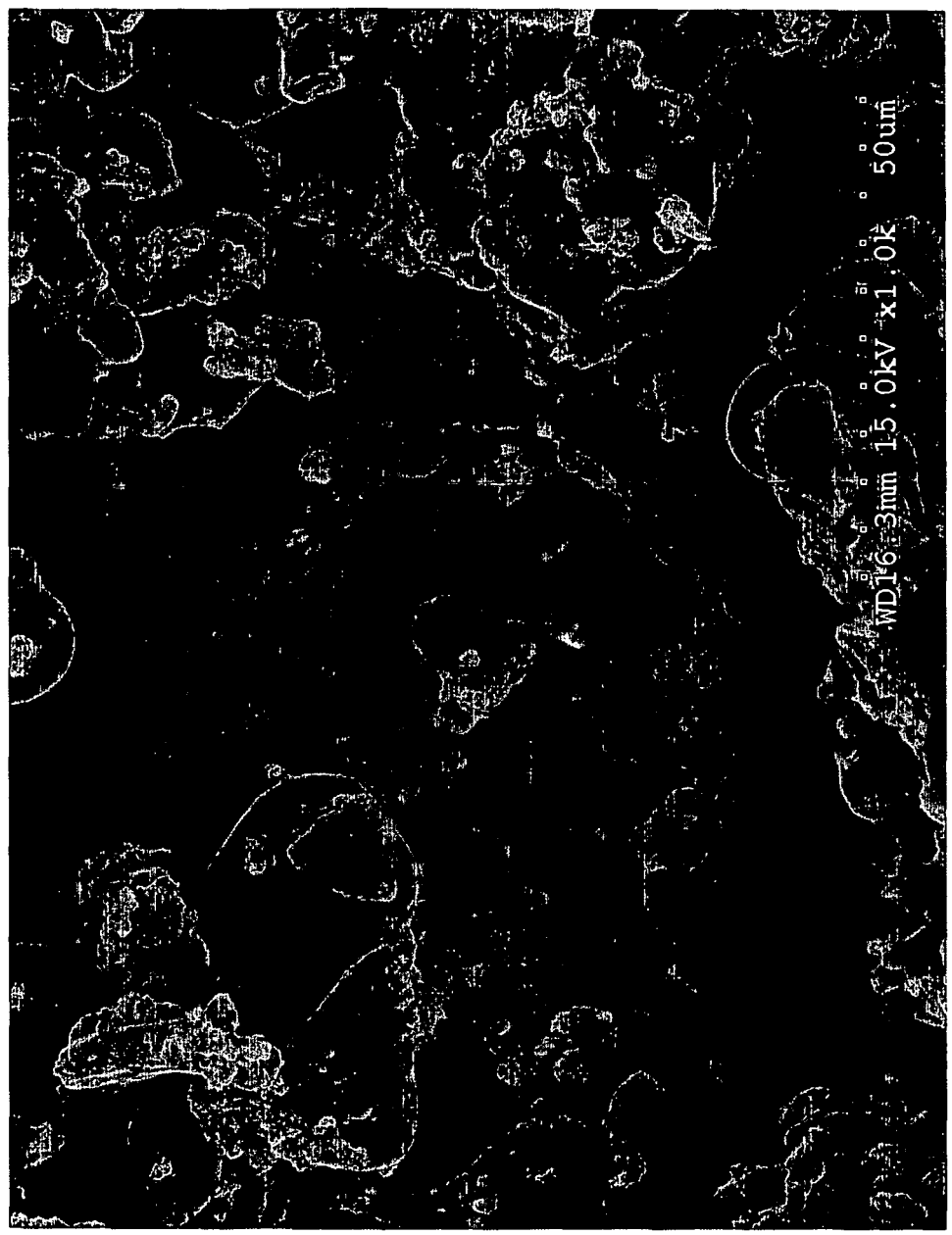
FIG. 13 is a SEM (1000×) of calcium-bound SRS-B prepared by extrusion with 20% calcium carbonate by weight based on starch.
Figure 22:
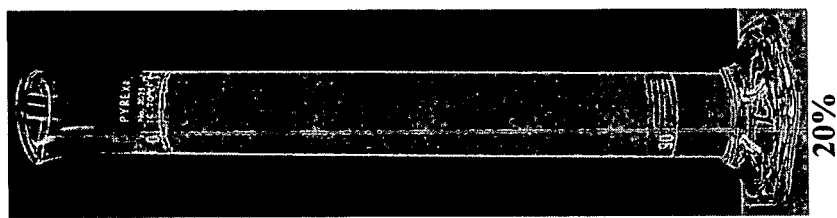
FIG. 22 shows the emulsion stability of calcium-bound SRS-B prepared by extrusion with calcium carbonate.
Figure 22:
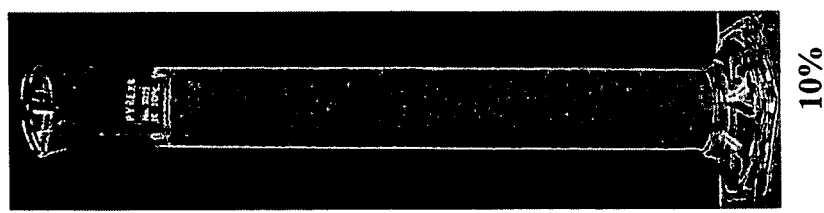

Calcium-bound starch was prepared with SRS-B and various levels of calcium carbonate by an extrusion process using the parameters shown in the table below. Ten parts SRS-B were mixed with calcium carbonate. Scanning electron microscopy showed mineral-bound SRS-B prepared by extrusion with calcium carbonate. FIGS. 12 and 13 shows SEMs of calcium-bound SRS-B prepared by extrusion with 10% and 20% calcium carbonate, respectively. In emulsion stability tests, mineral-bound starch products showed excellent emulsion stability and formed stable emulsions of calcium-bound starch, water and oil. FIG. 22 shows emulsion stabilities of calcium-bound SRS-B prepared by extrusion with calcium carbonate.

| SRS-B: Calcium carbonate | | |
| --- | --- | --- |
| Extrusion conditions | | |
| | 90:10 | 80:20 |
| Feed Rate | 160 lb/hr | 160 lb/hr |
| Extrusion Barrel Temperature Profile | 91-160-180-200-220° F. | 91-160-180-200-220° F. |
| Extrusion Pressure | 560 psi | 650 psi |
| Extrusion Motor Load | 25% | 22% |
| Extruder Speed | 450 rpm | 450 rpm |
| Moisture in the cylinder | 16 lb/hr | 16 lb/hr |
| Moisture in the barrel | 34 lb/hr | 40 lb/hr |
| Calcium content (mg/100 g starch) | | |
| | 90:10 | 80:20 |
| Before washing | 3400 | 6700 |
| After washing | 3170 | 6560 |

Example 11

Figure 14:
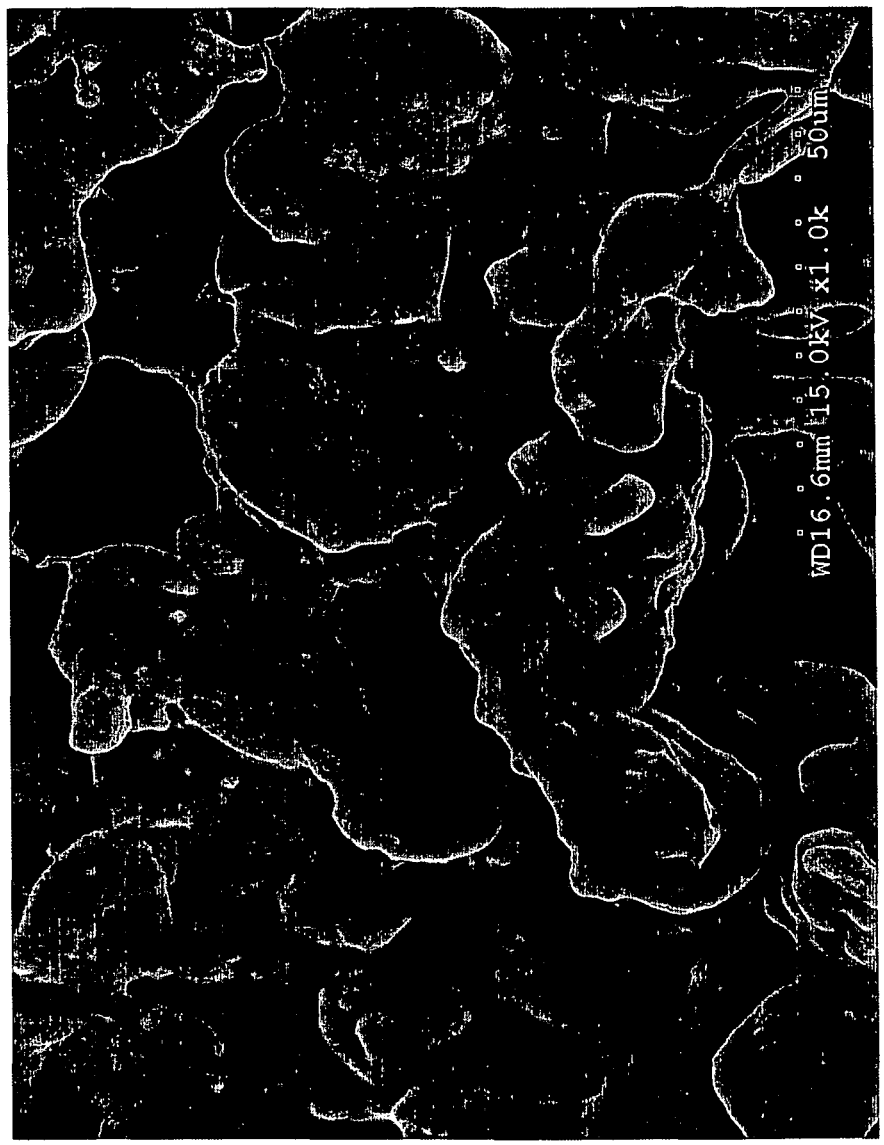
FIG. 14 is a SEM (1000×) of calcium-bound SRS-B prepared by extrusion with 10% calcium sulfate by weight based on starch.

Calcium-bound starch was prepared with SRS-B and calcium sulfate by an extrusion process using the parameters shown in the table below. Ten parts SRS-B were mixed with 1 part calcium sulfate. SEM showed mineral-bound SRS-B prepared by extrusion with calcium sulfate. FIG. 14 shows a SEM of calcium-bound SRS-B prepared by extrusion with 10% calcium sulfate. In emulsion stability tests, the extruded mineral-bound starch product showed excellent emulsion stability and formed stable emulsions of calcium-bound starch, water and oil.

| Extrusion conditions | |
| --- | --- |
| Feed Rate | 160 lb/hr |
| Extrusion Barrel Temperature Profile | 91-160-180-200-220° F. |
| Extrusion Pressure | 750 psi |
| Extrusion Motor Load | 20% |
| Extruder Speed | 450 rpm |
| Moisture in the cylinder | 16 lb/hr |
| Moisture in the barrel | 26 lb/hr |
| Calcium content (mg/100 g starch) | |
| Before washing | After washing |
| 2730 | 2420 |

Example 12

Figure 23:
FIG. 23 shows the emulsion stability of various mineral-bound SRS-B composites.

Iron was bound to SRS-B using ferrous ascorbate, ferric citrate or ferric sulfate according to the method of Example 1. Ten parts SRS-B were dispersed in 100 parts water and 1 part of an iron containing compound was added. The dispersion was warmed to 85° C. and maintained at that temperature for 1 hr with continuous stirring. The mineral-bound starch products were washed twice with excess water (10 ml) to remove unbound residues and dried at 40° C. In emulsion stability tests, mineral-bound starch products formed stable emulsions of iron-bound starch, water and oil. FIG. 23 shows emulsion stabilities of various mineral-bound SRS-B composites.

| Iron content (mg/100 g starch) after washing | |
| --- | --- |
| Ferrous ascorbate | 122 |
| Ferric citrate | 222 |
| Ferric sulfate | 1520 |

Example 13

Copper was bound by SRS-B using copper sulfate or copper gluconate according to the method of Example 11. In emulsion stability tests, mineral-bound starch products formed stable emulsions of copper-bound starch, water and oil. FIG. 23 shows the emulsion stability of copper-bound SRS-B prepared with copper gluconate.

| | Copper content (mg/100 g starch) after washing |
|---|---|
| Copper sulfate | 234 |
| Copper gluconate | 195 |

Example 14

Magnesium was bound to SRS-B with magnesium carbonate hydroxide, magnesium chloride, magnesium hydroxide, magnesium sulfate or magnesium stearate according to the method of Example 11. In emulsion stability tests, mineral-bound products formed stable emulsions of magnesium-bound starch, water and oil. FIG. 23 shows the emulsion stability of magnesium-bound SRS-B prepared with magnesium chloride.

| | Magnesium content (mg/100 g starch) |
|---|---|
| Magnesium carbonate hydroxide | 2500 |
| Magnesium chloride | 63 |
| Magnesium hydroxide | 3900 |
| Magnesium sulfate | 56 |
| Magnesium stearate | 135 |

Example 15

Manganese was bound to SRS-B with manganese sulfate according to the method of Example 11. In emulsion stability tests, mineral-bound starch products formed stable emulsions of manganese-bound starch, water and oil. FIG. 23 shows the emulsion stability of manganese-bound SRS-B prepared with manganese sulfate.

| | Manganese content (mg/100 g starch) after washing |
|---|---|
| Manganese sulfate | 181 |

Example 16

Zinc was bound by SRS-B with zinc chloride, zinc oxide, zinc stearate or zinc sulfate according to the method of Example 11. In emulsion stability tests, mineral-bound starch products formed stable emulsions of zinc-bound starch, water and oil. FIG. 23 shows the emulsion stability of zinc-bound SRS-B prepared with zinc chloride.

| | Zinc content (mg/100 g starch) after washing |
|---|---|
| Zinc chloride | 170 |
| Zinc oxide | 6880 |
| Zinc stearate | 326 |
| Zinc sulfate | 182 |

Example 17

Nickel was bound to SRS-B with nickel oxide according to the method of Example 11. In emulsion stability tests, mineral-bound starch products formed stable emulsions of nickel-bound starch, water and oil. FIG. 23 shows the emulsion stability of nickel-bound SRS-B prepared with nickel oxide.

| | Nickel content (mg/100 g starch) after washing |
|---|---|
| Nickel oxide | 2640 |

Example 18

Sodium was bound to SRS-B with sodium citrate according to the method of Example 11. In emulsion stability tests, mineral-bound starch products formed stable emulsions of sodium-bound starch, water and oil. FIG. 23 shows the emulsion stability of sodium-bound SRS-B prepared with sodium citrate.

| | Sodium content (mg/100 g starch) after washing |
|---|---|
| Sodium citrate | 117 |

Example 19

Potassium was bound to SRS-B with potassium iodide according to the method of Example 11. In emulsion stability tests, mineral-bound starch products formed stable emulsions of potassium-bound starch, water and oil. FIG. 23 shows the emulsion stability of potassium-bound SRS-B prepared with potassium iodide.

| | Potassium content (mg/100 g starch) after washing |
|---|---|
| Potassium iodide | 85 |

Changes may be made in the above methods and systems without departing from the invention described in the Summary and defined by the following claims. It should thus be noted that the matter contained in the above description or shown in the accompanying drawings should be interpreted as illustrative and not limiting.

All references cited are incorporated by reference herein.

We claim:

1. An edible starch comprising a plurality of individual, cross-linked, gelatinized starch granules having at least one dietary mineral bound both evenly within the internal structure of the starch granules and on the surface of the starch granules, wherein the granules retain the at least one dietary mineral throughout hot and cold water hydration cycling, but release the at least one dietary mineral after consumption and digestion of the starch granules.

2. The starch of claim 1, wherein said starch granules are derived from the group of starch sources consisting of cereal, root, tuber, legume, and mixtures thereof.

3. The starch of claim 2, wherein said starch granules are derived from the group of starch sources consisting of wheat, waxy wheat, corn, waxy corn, high amylose corn, oat, rice, tapioca, mung bean, sago, sweet potato, potato, barley, triticale, sorghum, banana, and mixtures thereof.

4. The starch of claim 2, wherein said starch granules are cross-linked by a crosslinker selected from the group consisting of phosphorylating agents and epichlorohydrin.

5. The starch of claim 4, wherein said crosslinker is selected from the group consisting of sodium trimetaphosphate, sodium tripolyphosphate and mixtures thereof.

6. The starch of claim 1, wherein said starch granules are oxidized.

7. The starch of claim 6, wherein said granules are oxidized by an oxidizing agent selected from the group consisting of periodate, chromic acid, permanganate, nitrogen dioxide, sodium hypochlorite and mixtures thereof.

8. The starch of claim 1 further comprising at least about 1.0% by weight of the at least one mineral.

9. The starch of claim 1 further comprising at least about 5% by weight of the at least one mineral.

10. The starch of claim 1 further comprising at least about 10% by weight of the at least one mineral.

11. The starch of claim 1, wherein the at least one mineral is selected from the group consisting of aluminum, calcium, copper, iron, iodine, magnesium, manganese, nickel, potassium, chromium, zinc, sodium and mixtures thereof.

12. The starch of claim 1, wherein said starch granules are stable during successive washing with excess water without the loss of more than about 2% mineral content.

13. The starch of claim 1, wherein said starch granules have upon swelling thereof a swelling power in cold water which is at least about 200% greater than the swelling power of unmodified granular starch.

14. The starch of claim 1, wherein said starch granules have upon swelling thereof in cold water a swelling power which is at least about 400% greater than the swelling power of unmodified granular starch.

15. The starch of claim 1, wherein an oil:water emulsion formed by said starch granules has a stability of at least about 1 ml/g.

16. The starch of claim 1, wherein said starch granules are at least about 80% digested by AOAC method 991.43 (2003).

17. The starch of claim 1, wherein said starch granules are at least about 90% digested by AOAC method 991.43 (2003).

18. A food product including therein the starch of claim 1.

19. A cosmetic or personal care product including therein the starch of claim 1.

20. A method of preparing the edible starch of claim 1, said method comprising:
forming a dispersion of starch granules in water, said granules undergoing swelling in said dispersion and having a crystalline phase;
adding a cross-linking agent to said dispersion while said granules are swelled;
cross-linking the swelled starch granules under conditions of continuous stirring;
said cross-linking step being carried out without complete gelatinization of said swelled starch granules;
recovering said cross-linked starch granules;
forming a second dispersion comprising said cross-linked starch granules and at least one dietary mineral; and
heating said second dispersion in order to melt the crystalline phase of said granules.

21. The method of claim 20, further comprising the steps of isolating the starch granules, and
mixing the isolated starch granules with a food composition.

22. The method of claim 20, further comprising the steps of isolating the starch granules, and
mixing the isolated starch granules with a cosmetic or personal care composition.

23. An edible starch comprising a plurality of individual, cross-linked, gelatinized starch granules having at least one dietary mineral bound both evenly within the internal structure of the starch granules and on the surface of the starch granules, wherein the granules retain the at least one dietary mineral while undergoing multiple cycles of swelling in 95° C. water for a period of 30 minutes followed by drying at 105° C. to a moisture content of less than about 10% by weight, wet basis, but release the at least one dietary mineral after consumption and digestion of the starch granules.

24. The starch of claim 23, wherein said starch granules are derived from the group of starch sources consisting of cereal, root, tuber, legume and mixtures thereof.

25. The starch of claim 24, wherein said starch granules are derived from the group of starch sources consisting of wheat, waxy wheat, corn, waxy corn, high amylose corn, oat, rice, tapioca, mung bean, sago, sweet potato, potato, barley, triticale, sorghum, banana and mixtures thereof.

26. The starch of claim 23, wherein said granules are cross-linked by a crosslinker selected from the group consisting of phosphorylating agents and epichlorohydrin.

27. The starch of claim 26, wherein said crosslinker is selected from the group consisting of sodium trimetaphosphate, sodium tripolyphosphate and mixtures thereof.

28. The starch of claim 23, wherein said starch granules are oxidized.

29. The starch of claim 28, wherein said granules are oxidized by an oxidizing agent selected from the group consisting of periodate, chromic acid, permanganate, nitrogen dioxide, sodium hypochlorite and mixtures thereof.

30. The starch of claim 23 further comprising at least about 1.0% by weight of said at least one mineral.

31. The starch of claim 23 further comprising at least about 5% by weight of said at least one mineral.

32. The starch of claim 23 further comprising at least about 10% by weight of said at least one mineral.

33. The starch of claim 23, wherein said at least one mineral is selected from the group consisting of aluminum, calcium, copper, iron, iodine, magnesium, manganese, nickel, potassium, chromium, zinc, sodium and mixtures thereof.

34. The starch of claim 23, wherein said starch granules are stable during successive washing with excess water without the loss of more than about 2% by weight mineral content.

35. The starch of claim 23, wherein said starch granules have upon swelling thereof a swelling power in cold water which is at least about 200% greater than the swelling power of unmodified granular starch.

36. The starch of claim 23, wherein said starch granules have upon swelling thereof in cold water a swelling power which is at least about 400% greater than the swelling power of unmodified granular starch.

37. The starch of claim 23, wherein an oil:water emulsion formed by said starch granules has a stability of at least about 1 ml/g.

38. The starch of claim 23, wherein an oil:water emulsion formed by said starch granules has a stability of at least about 5 ml/g.

39. The starch of claim 23, wherein said starch granules are at least about 80% digested by AOAC method 991.43 (2003).

40. The starch of claim 23, wherein said starch granules are at least about 90% digested by AOAC method 991.43 (2003).

41. A food product including therein the starch of claim 23.

42. A cosmetic or personal care product including therein the starch of claim 23.

* * * * *